(12) United States Patent
Li et al.

(10) Patent No.: US 12,359,186 B2
(45) Date of Patent: Jul. 15, 2025

(54) METHOD FOR PREPARING MULTISUBUNIT SCF E3 LIGASE WITH FUSION PROTEIN THROUGH IN VITRO RECONSTITUTION, AND USE OF MULTISUBUNIT SCF E3 LIGASE

(71) Applicant: Institute of Genetics and Developmental Biology, CAS, Beijing (CN)

(72) Inventors: Jiayang Li, Beijing (CN); Bing Wang, Beijing (CN); Huihui Liu, Beijing (CN); Hong Yu, Beijing (CN); Xiangbing Meng, Beijing (CN); Guifu Liu, Beijing (CN); Mingjiang Chen, Beijing (CN); Yanhui Jing, Beijing (CN)

(73) Assignee: Institute of Genetics and Developmental Biology, CAS (CN)

( * ) Notice: Subject to any disclaimer, the term of this patent is extended or adjusted under 35 U.S.C. 154(b) by 49 days.

(21) Appl. No.: 18/323,983

(22) Filed: May 25, 2023

(65) Prior Publication Data
US 2023/0407287 A1    Dec. 21, 2023

(30) Foreign Application Priority Data
Jun. 20, 2022   (CN) .......................... 202210696862.7

(51) Int. Cl.
*C12N 9/00*    (2006.01)
*C07K 14/47*   (2006.01)

(52) U.S. Cl.
CPC ............ *C12N 9/93* (2013.01); *C07K 14/4702* (2013.01)

(58) Field of Classification Search
CPC ........ C12N 9/93; C12N 5/0601; C12N 15/86; C12N 2510/00; C12N 2710/14043; C12N 15/62; C12N 15/85; C07K 14/4702; C07K 14/001; C07K 2319/00; C12Y 603/02019
See application file for complete search history.

(56) References Cited

PUBLICATIONS

Starita et al. (PNAS, 2013, 110(14):E1263-E1272) (Year: 2013).*
Harper et al. (Ann Rev Biochem, 2021, 90:403:429) (Year: 2021).*
Starita SI (supplemental information to Starita et al., 2013, 12 pages) (Year: 2013).*
UniProt Database Accession No. Q9ES00 (https://rest.uniprot.org/unisave/Q9ES00?format=txt&versions=101, Sep. 2013, 4 pages) (Year: 2013).*

* cited by examiner

*Primary Examiner* — David Steadman
*Assistant Examiner* — Joseph R Spangler
(74) *Attorney, Agent, or Firm* — Calderon Safran & Wright P.C.; Corinne Marie Pouliquen

(57) ABSTRACT

The disclosure discloses a method for preparing a multisubunit SCF E3 ligase with a fusion protein through in vitro reconstitution, and a use of the multisubunit SCF E3 ligase. The method for preparing a multisubunit SCF E3 ligase with a fusion protein through in vitro reconstitution disclosed by the disclosure includes: subjecting an engineered SKP1-Cullin1-RBX1 fusion protein (referred to as eSCR) to a reaction with an F-box protein in a reaction system to obtain the multisubunit SCF E3 ligase, where the eSCR fusion protein has an amino acid sequence from position 10 to position 1062 of SEQ ID NO: 2. Experimental results show that different multisubunit SCF E3 ligases are successfully prepared with the eSCR fusion protein through in vitro reconstitution in the disclosure; the reconstituted multisubunit E3 ligase has biological activity.

7 Claims, 11 Drawing Sheets
Specification includes a Sequence Listing.

FIG. 1A

Flag-SKP1-Cullin1-RBX1-myc (Flag-eSCR-myc)

MDYKDDDDKMAAEAETKAMITLRSCEGQVPEVAEAVAMESQTIRHMIEDKCADTGIPLPNVSAKILSKVI
EYCSRHVEARGGAAAAADGDAPAPAAVEANKAVEDELKTPDAEFVKVDQSTLFDLILAANYLNIKGLLDL
TCQTVADMIKGKIPEEIRKTFNIKNDFTPEEEHEVRRENQWAFEGGSGMATHERKTIDLEQGWEPMQKGI
TKLKNILEGKPEPQFSSEDYMMLYTTIYNMCTQKPPHDYSQQLYEKYRESFEEYITSMVLPSLREKHDEF
MLRELVKRWSNHKVMVRWLSRFFHYLDRYFISRRSLPQLSEVGLSCFRDLVYQEIKGKVKSAVISLIDQE
REGEQIDRALLKNVLDIFVEIGLTSMDYYENDFEDFLLKDTADYYSIKAQTWILEDSCPDYMLKAEECLK
REKERVAHYLHSSSEQKLLEKVQHELLTQYASQLLEKEHSGCHALLRDDKVDDLSRMYRLFSRITRGLEP
VSQIFKQHVTNEGTALVKQAEDAASNKKPEKKEIVGLQEQVFVRKIIELHDKYVAYVTDCFQGHTLFHKA
LKEAFEVCNKGVSGSSSAELLATFCDNILKKGGSEKLSDEAIEDTLEKVVRLLAYISDKDLFAEFYRKK
LARRLLFDKSANDEHERSILTKLKQQCGGQFTSKMEGMVTDLTVARDHQAKFEEFISTHSELNPGIALAV
TVLTTGFWPSYKSFDINLPAEMVKCVEVFKEFYQTRTKHRKLTWIYSLGTCNINAKFEAKTIELIVTTYQ
AALLLLFNGVDRLSYSEIVTQLNLSDDDVVRLLHSLSCAKYKILSKEPNNRSISPNDVFEFNSKFTDKLR
RLKIPLPPVDEKKKVVEDVDKDRRYAIDASIVRIMKSRKVLGHQQLVMECVEQLGRMFKPDFKAIKKRIE
DLITRDYLERDKDNPNVYRYLAGGSGMSAMETDINAPPPPAPAPAGAGEGSSSAAGPSSRKPNKRPEIKK
WNAVALWAWDIVVDNCAICRNHIMDLCIECQANQASATSEECTVAWGVCNHAFHFHCISRWLKTRQVCPL
DNSEWEFQKYGHEQKLISEEDL

FIG. 1B

METHOD FOR PREPARING MULTISUBUNIT SCF E3 LIGASE WITH FUSION PROTEIN THROUGH IN VITRO RECONSTITUTION, AND USE OF MULTISUBUNIT SCF E3 LIGASE

CROSS REFERENCE TO RELATED APPLICATION

This patent application claims the benefit and priority of Chinese Patent Application No. 202210696862.7, filed with the China National Intellectual Property Administration on Jun. 20, 2022, the disclosure of which is incorporated by reference herein in its entirety as part of the application.

REFERENCE TO AN ELECTRONIC SEQUENCE LISTING

A computer readable XML file entitled "GWP20221202172_seglist.xml", that was created on Apr. 23, 2023, with a file size of about 53,759 bytes, contains the sequence listing for this application, has been filed with this application, and is hereby incorporated by reference in its entirety.

FIELD OF THE INVENTION

The disclosure belongs to the field of biotechnology, and relates to a method for preparing a multisubunit SCF E3 ligase with a fusion protein through in vitro reconstitution, and a use of the multisubunit SCF E3 ligase.

BACKGROUND OF THE INVENTION

Protein degradation plays an important role in maintaining normal function of cells and organisms. In eukaryotes, there are two major pathways for protein degradation: lysosome-dependent pathway and ubiquitin-proteasome dependent pathway. The ubiquitin-proteasome dependent pathway is composed of substrate ubiquitination and subsequent degradation by proteasome, and plays essential roles in regulating various biological processes, including cell proliferation, cell differentiation, apoptosis, DNA replication and repair, transcription, signal transduction, and protein quality control. In plants, many proteins that control important cell biological processes are regulated by the ubiquitin-proteasome system (UPS), such as the key factor TIR1 in the auxin signaling pathway, the key factor COI1 in the jasmonic acid (JA) signaling pathway, the key factor GID2 in the gibberellin (GA) signaling pathway, and the key factors D14 and D53 in the strigolactone (SL) signaling pathway. Protein ubiquitination requires the concerted reactions of ubiquitin-activating enzyme (UAE, E1), ubiquitin-conjugating enzyme (UCE, E2), and ubiquitin ligase (E3). The multisubunit SCF E3 ligase consists of SKP1, Cullin1, RBX1, and an interchangeable F-box protein. In higher plants, multisubunit SCF E3 ligases play a crucial role in regulation of plant growth and development and responses to environmental stresses.

In vitro ubiquitination analysis system plays an important role in elucidating molecular mechanism of an E3 ligase or a substrate protein in plant growth and development. So far, there has been still no research on the preparation of functional multisubunit E3 ligases in vitro in plants, which greatly limits the investigation of molecular mechanisms of multisubunit E3 ligases. In order to elucidate the mechanism of multisubunit SCF E3 ligase, it is necessary to establish and optimize an in vitro reconstitution system of multisubunit SCF E3 ligase. However, in vitro reconstitution of functional multisubunit SCF E3 ligase remains a challenge, mainly due to difficulties in achieving active subunits of complex SCF E3 ligase with high purity. Establishing the in vitro reconstitution platform for multisubunit SCF E3 ligase using an engineered SKP1-Cullin1-RBX1 fusion protein (eSCR) is of great biological significance, and also provides a powerful tool to elucidate molecular mechanisms of multisubunit E3 ligase in plants.

SUMMARY OF THE INVENTION

The technical problem to be solved by the disclosure is to prepare an active multisubunit SCF E3 ligase in vitro.

In order to solve the technical problem above, the disclosure first provides a preparation method of an active multisubunit SCF E3 ligase, including: addition of an eSCR fusion protein to a reaction with an F-box protein in the reaction system to achieve active multisubunit SCF E3 ligases.

The eSCR fusion protein is selected from the group consisting of A1), A2), and A3):

A1) a fusion protein with an amino acid sequence from position 10 to position 1062 of SEQ ID NO: 2;

A2) a protein that is obtained through substitution and/or deletion and/or addition of one or more amino acid residues based on the amino acid sequence from position 10 to position 1062 of SEQ ID NO: 2 and has the same function as the amino acid sequence from position 10 to position 1062 of SEQ ID NO: 2; and A3) a fusion protein obtained by linking a tag to an N-terminus and/or a C-terminus of A1) or A2).

A sequence from position 10 to position 184 of SEQ ID NO: 2 is an amino acid sequence of the SKP1 protein; a sequence from position 189 to position 932 of SEQ ID NO: 2 is an amino acid sequence of the Cullin1 protein; a sequence from position 937 to position 1062 of SEQ ID NO: 2 is an amino acid sequence of the RBX1 protein; a sequence from position 185 to position 188 of SEQ ID NO: 2 is a linker sequence between the SKP1 protein and the Cullin1 protein; and a sequence from position 933 to position 936 of SEQ ID NO: 2 is a linker sequence between the Cullin1 protein and the RBX1 protein.

To facilitate the purification of the protein in A1), a tag shown in Table 1 can be linked to an N-terminus or C-terminus of the protein with an amino acid sequence from position 10 to position 1062 of SEQ ID NO: 2 in the sequence listing.

TABLE 1

| Tag Sequences | | |
|---|---|---|
| Tag | Residue | Sequence |
| Poly-Arg | 5 to 6 (usually 5) | RRRRR (SEQ ID NO: 3) |
| Poly-His | 2 to 10 (usually 6) | HHHHHH (SEQ ID NO: 4) |
| Flag | 8 | DYKDDDDK (SEQ ID NO: 5) |
| Strep-tag II | 8 | WSHPQFEK (SEQ ID NO: 6) |
| c-myc | 10 | EQKLISEEDL (SEQ ID NO: 7) |

The eSCR fusion protein described in A2) has 75% or more identity with the amino acid sequence from position 10 to position 1062 of SEQ ID NO: 2 and has the same function as the eSCR fusion protein. The 75% or more identity refers to 75%, 80%, 85%, 90%, 95%, 96%, 97%, 98%, or 99% identity.

The eSCR fusion protein described in A2) can be artificially synthesized, or a coding gene of the fusion protein can be first synthesized and then the fusion protein is biologically expressed.

The coding gene of the eSCR fusion protein described in A2) can be obtained by deletion of codon(s) of one or more amino acid residues from a DNA sequence from position 28 to position 3186 of SEQ ID NO: 1, and/or missense mutation of one or more base pairs from the DNA sequence, and/or linking a coding sequence of a tag shown in Table 1 to a 5'-terminus and/or a 3'-terminus of the DNA sequence. A DNA sequence from position 28 to position 3186 of SEQ ID NO: 1 encodes the eSCR fusion protein from position 10 to position 1062 of SEQ ID NO: 2.

A sequence from position 28 to position 552 of SEQ ID NO: 1 is a nucleotide sequence encoding the SKP1 protein; a sequence from position 565 to position 2796 of SEQ ID NO: 1 is a nucleotide sequence encoding the Cullin1 protein; a sequence from position 2809 to position 3186 of SEQ ID NO: 1 is a nucleotide sequence encoding the RBX1 protein; and a sequence from position 553 to position 564 of SEQ ID NO: 1 and a sequence from position 2797 to position 2808 of SEQ ID NO: 1 are nucleotide sequences encoding linker sequences.

Specifically, the fusion protein described in A3) may be a protein shown in SEQ ID NO: 2.

In the method described above, the reaction system may further include 50 mM Tris-HCl buffer (pH 7.4), MgCl$_2$, DTT, and/or ATP;

and/or, the reaction may be conducted at 22° C. to 37° C., such as 28° C.; and and/or, the reaction may be conducted for 1 h to 2 h.

Specifically, the reaction system may be obtained by adding MgCl$_2$, ATP, DTT, the eSCR fusion protein to 50 mM Tris-HCl buffer (pH 7.4), and a content of each component in the reaction system may be as follows: MgCl$_2$: 10 mM, DTT: 2 mM, ATP: 5 mM, and eSCR fusion protein: 0.8 g/30 L.

In an embodiment of the disclosure, the F-box protein is D3 or D3 with a tag.

In an embodiment of the disclosure, the F-box protein is GID2 or GID2 with a tag.

In an embodiment of the disclosure, the F-box protein is FBXL18 or FBXL18 with a tag.

In an embodiment of the disclosure, the F-box protein is CDC4 or CDC4 with a tag.

An E3 ligase prepared by the preparation method of a multisubunit SCF E3 ligase also falls within the protection scope of the disclosure.

The disclosure also provides a preparation method of a polyubiquitin chain, including: subjecting the eSCR fusion protein, an F-box protein, a UAE E1, a UCE E2, and a ubiquitin monomer to the reaction system to obtain the polyubiquitin chain. The polyubiquitin chain (or ubiquitin chain) refers to a ubiquitin chain formed by two or more ubiquitin moieties.

The disclosure also provides an in vitro preparation method of a ubiquitinated target protein, including: subjecting a target protein, the eSCR fusion protein described above, an F-box protein, a UAE E1, a UCE E2, and a ubiquitin monomer to the reaction system to obtain the ubiquitinated target protein.

In the method described above, the reaction system may further include 50 mM Tris-HCl buffer (pH 7.4), MgCl$_2$, DTT, and/or ATP;

and/or, the reaction may be conducted at 22° C. to 37° C., such as 28° C.; and and/or, the reaction may be conducted for 1 h to 2 h.

Specifically, the reaction system for preparing the ubiquitin chain may be obtained by adding MgCl$_2$, DTT, ATP, the eSCR fusion protein, an F-box protein, an UAE E1, an UCE E2, and an ubiquitin monomer to 50 mM Tris-HCl buffer (pH 7.4), and a content of each component in the reaction system may be as follows: MgCl$_2$: 10 mM, DTT: 2 mM, ATP: 5 mM, eSCR fusion protein: 0.8 g/30 L, UAE E1: 50 ng/30 L, UCE E2: 200 ng/30 L, and Ubiquitin: 5 g/30 L.

Specifically, the reaction system for preparing the ubiquitinated target protein may be obtained by adding MgCl$_2$, DTT, ATP, the eSCR fusion protein, an F-box protein, an UAE E1, an UCE E2, an ubiquitin monomer, and a target protein to 50 mM Tris-HCl buffer (pH 7.4), and a content of each component in the reaction system may be as follows: MgCl$_2$: 10 mM, DTT: 2 mM, ATP: 5 mM, eSCR fusion protein: 0.8 g/30 L, UAE E1: 50 ng/30 L, UCE E2: 200 ng/30 L, Ubiquitin: 5 g/30 L, and target protein: 100 ng/30 L.

In an embodiment of the disclosure, the UAE E1 is *Oryza sativa* L. EL.

In an embodiment of the disclosure, the UAE E1 is human E1.

In an embodiment of the disclosure, the UCE E2 is OsUBC14.

In an embodiment of the disclosure, the UCE E2 is HsUbcH5C.

In an embodiment of the disclosure, the UCE E2 is HsCDC34.

The ubiquitin monomer may be a ubiquitin monomer of a corresponding species.

In an embodiment of the disclosure, the target protein may be D53-HA.

In an embodiment of the disclosure, the target protein may be Sic1-HA.

The disclosure also provides a reagent kit, including the eSCR fusion protein and the F-box protein.

The reagent kit may further include 50 mM Tris-HCl buffer (pH 7.4), MgCl$_2$, DTT, ATP, UAE E1, UCE E2, and/or a ubiquitin monomer.

The reagent kit may be composed only of the eSCR fusion protein and the F-box protein, and may also be composed of the eSCR fusion protein, the F-box protein, and at least one selected from the group consisting of the following: 50 mM Tris-HCl buffer (pH 7.4), MgCl$_2$, DTT, ATP, UAE E1, UCE E2, and a ubiquitin monomer.

The reagent kit may be used to prepare an E3 ligase and may also be used to prepare a ubiquitin chain or a ubiquitinated target protein.

The eSCR fusion protein or a biological material associated with the eSCR fusion protein also belongs to the protection scope of the disclosure, where the biological material is any one selected from the group consisting of B1) to B5):

B1) a nucleic acid encoding the eSCR fusion protein;
B2) an expression cassette carrying the nucleic acid described in B1);
B3) a recombinant vector carrying the nucleic acid described in B1) or a recombinant vector carrying the expression cassette described in B2);
B4) a recombinant microorganism carrying the nucleic acid described in B1), a recombinant microorganism carrying the expression cassette described in B2), or a recombinant microorganism carrying the recombinant vector described in B3); and B5) a cell line carrying the nucleic acid described in B1), a cell line carrying the expression cassette described in B2), or a cell line carrying the recombinant vector described in B3).

The nucleic acid described in B1) may be selected from the group consisting of b11), b12), b13), b14), or b15):

b11) a cDNA or DNA molecule with a coding sequence from position 28 to position 3186 of SEQ ID NO: 1 in the sequence listing;

b12) a DNA molecule from position 28 to position 3186 of SEQ ID NO: 1 in the sequence listing;

b13) a DNA molecule shown in SEQ ID NO. 1 in the sequence listing;

b14) a cDNA or DNA molecule that has 75% or more identity with the nucleotide sequence defined in b11), b12), or b13) and encodes the eSCR fusion protein; and b15) a cDNA or DNA molecule that can hybridize with the nucleotide sequence defined in b11), b12), b13), or b14) under strict conditions and encodes the eSCR fusion protein.

The nucleic acid can be DNA, such as cDNA, genomic DNA (gDNA), or recombinant DNA; and the nucleic acid can also be RNA, such as mRNA or hnRNA.

Those of ordinary skill in the art can easily conduct mutation on the nucleotide sequence encoding the eSCR fusion protein of the disclosure using a known method such as site-directed mutation. As long as those artificially-modified nucleotide sequences that have 75% or more identity with the nucleotide sequence encoding the eSCR fusion protein isolated in the disclosure can encode the eSCR fusion protein and have the function of the eSCR fusion protein, they are all derived from and equivalent to the nucleotide sequence of the disclosure.

The term "identity" used herein refers to sequence similarity to a natural nucleic acid sequence. The "identity" includes 75% or more, 85% or more, 90% or more, or 95% or more identity with the nucleotide sequence encoding the eSCR fusion protein of the disclosure. The identity can be evaluated by naked eyes or computer software. When computer software is used, the identity among two or more sequences can be expressed as a percentage (%), which can be used to evaluate the identity among related sequences.

The strict conditions may be as follows: hybridizing at 50° C. in a mixed solution of 7% sodium dodecyl sulfate (SDS), 0.5 M NaPO$_4$, and 1 mM ethylenediaminetetraacetic acid (EDTA), and rinsing at 50° C. with 2×saline sodium citrate (SSC) and 0.1% SDS; the strict conditions may also be as follows: hybridizing at 50° C. in a mixed solution of 7% SDS, 0.5 M NaPO$_4$, and 1 mM EDTA, and rinsing at 50° C. with 1×SSC and 0.1% SDS; the strict conditions may also be as follows: hybridizing at 50° C. in a mixed solution of 7% SDS, 0.5 M NaPO$_4$, and 1 mM EDTA, and rinsing at 50° C. with 0.5×SSC and 0.1% SDS; the strict conditions may also be as follows: hybridizing at 50° C. in a mixed solution of 7% SDS, 0.5 M NaPO$_4$, and 1 mM EDTA, and rinsing at 50° C. with 0.1×SSC and 0.1% SDS; the strict conditions may also be as follows: hybridizing at 50° C. in a mixed solution of 7% SDS, 0.5 M NaPO$_4$, and 1 mM EDTA, and rinsing at 65° C. with 0.1×SSC and 0.1% SDS; the strict conditions may also be as follows: hybridizing at 65° C. in a solution of 6×SSC and 0.5% SDS, and then rinsing with 2×SSC and 0.1% SDS once and with 1×SSC and 0.1% SDS once; the strict conditions may also be as follows: hybridizing at 68° C. in a solution of 2×SSC and 0.1% SDS, then rinsing at 68° C. for 5 min twice, hybridizing at 68° C. in a solution of 0.5×SSC and 0.1% SDS, and rinsing at 68° C. for 15 min twice; and the strict conditions may also be as follows: hybridizing at 65° C. in a solution of 0.1×SSPE (or 0.1×SSC) and 0.1% SDS, and then rinsing.

The 75% or more identity mentioned above may be 80%, 85%, 90%, or 95% or more identity.

The expression cassette carrying the nucleic acid encoding the eSCR fusion protein (eSCR gene-expressing cassette) described in B2) refers to DNA capable of expressing the eSCR fusion protein in a host cell, which may include a promoter to initiate the transcription of the eSCR gene and a terminator to terminate the transcription of the eSCR gene. Further, the expression cassette may further include an enhancer sequence.

The recombinant vector carrying the eSCR gene-expressing cassette may be constructed using the existing expression vector.

In the use above, the vector may be selected from the group consisting of a plasmid, a bacmid, a phage, and a viral vector. The plasmid may be specifically a pFastBac Dual vector.

The recombinant vector described in B3) may be specifically a Flag-SKP1-Cullin1-RBX1-myc vector. The Flag-SKP1-Cullin1-RBX1-myc vector may be a recombinant vector obtained by substituting a DNA fragment between EcoRI and SpeI endonuclease recognition sequences of the pFastBac Dual vector with the eSCR fusion gene from position 1 to position 3219 of SEQ ID NO: 1 in the sequence listing.

The microorganism may be selected from the group consisting of yeast, bacteria, algae, and fungi.

The cell line may be a Sf9 insect cell line. The cell line does not include a propagating material.

The disclosure also provides any use selected from the group consisting of the following, which also fall within the protection scope of the disclosure:

X1) a use of the multisubunit SCF E3 ligase in the preparation of a ubiquitin chain or a ubiquitinated target protein;

X2) a use of the multisubunit SCF E3 ligase in the production of a product for preparing a ubiquitin chain or a ubiquitinated target protein;

X3) a use of the reagent kit in the preparation of a multisubunit SCF E3 ligase;

X4) a use of the reagent kit in the production of a product for preparing a multisubunit SCF E3 ligase;

X5) a use of the reagent kit in the preparation of a ubiquitin chain or a ubiquitinated target protein;

X6) a use of the reagent kit in the production of a product for preparing a ubiquitin chain or a ubiquitinated target protein;

X7) a use of the eSCR fusion protein or the biological material in the preparation of a multisubunit SCF E3 ligase;

X8) a use of the eSCR fusion protein or the biological material in the production of a product for preparing a multisubunit SCF E3 ligase;

X9) a use of the eSCR fusion protein or the biological material in the preparation of a ubiquitin chain or a ubiquitinated target protein; and X10) a use of the eSCR fusion protein or the biological material in the production of a product for preparing a ubiquitin chain or a ubiquitinated target protein.

Different multisubunit SCF E3 ligases are successfully prepared with the eSCR fusion protein through in vitro reconstitution in the disclosure; the E3 ligase has biological activity; and the disclosure has a wide range of potential applications in elucidating molecular mechanism of a multisubunit SCF E3 ligase.

The disclosure will be described in further detail below with reference to specific examples.

The examples given are only for the purpose of illustrating the disclosure, and are not intended to limit the scope of the disclosure. The examples provided below can serve as a guide for further improvement by those of ordinary skill in the art, and are not intended to limit the disclosure in any way.

BRIEF DESCRIPTION OF THE DRAWINGS

FIGS. 1A-B are schematic diagrams of a fusion protein Flag-eSCR-myc, where FIG. 1A shows a schematic diagram of the fusion protein Flag-SKP1-Cullin1-RBX1-myc (Flag-eSCR-myc); FIG. 1B shows the amino acid sequence information of the fusion protein Flag-SKP1-Cullin1-RBX1-myc; and Flag-eSCR-myc represents an engineered fusion protein Flag-SKP1-Cullin1-RBX1-myc.

FIG. 2A shows the Coomassie brilliant blue (CBB) staining quantification (left panel) and western blotting (WB) (right panel) results of the fusion protein expressed and purified in the baculovirus expression system; FIG. 2B shows the NEDD8 modification on the Cullin1 protein in the fusion protein eSCR, and the experimental results show that the fusion protein eSCR has the NEDD8 modification, while the NEDD8 modification on the $eSC^{K6884}R$ fusion protein is deleted, indicating that the fusion protein eSCR used in this study is biologically active; and FIG. 2C shows the experimental results of detecting the self-ubiquitination activity of the fusion protein eSCR in an in vitro activity assay system (the anti-Ub antibody can recognize a signal of NEDD8 through a cross reaction, and the Cullin1 protein in the Flag-eSCR-myc protein has the NEDD8 modification and thus can also be recognized by the anti-Ub antibody), and the experimental results show that the fusion protein Flag-eSCR-myc does not have self-ubiquitination activity in the in vitro activity assay system.

FIG. 5A shows the experimental results of D53's ubiquitination by the $eSCF^{D3}$ E3 ligase, and the experimental results show that the $eSCF^{D3}$ E3 ligase can effectively ubiquitinate the protein D53 in the presence of OsE1, OsUbiquitin, and OsUBC14; and FIG. 5B shows that, addition of strigolactone receptor protein TRX-D14 and strigolactone analog rac-GR24, the ubiquitination level of D53 by the $eSCF^{D3}$ E3 ligase is enhanced, and the experimental results show that the $eSCF^{D3}$ E3 ligase has the same sensitivity as the WT $SCF^{D3}$ E3 ligase and thus can be used to detect the strigolactone signal transduction, which provides a powerful technical analysis platform for studying the strigolactone signaling pathway.

FIG. 8A shows the preparation of an $eSCF^{FBXL18}$ E3 ligase with the fusion protein Flag-eSCR-myc and a human-derived FBXL18 protein through in vitro reconstitution, and the experimental results show that, in the presence of HsE1, HsUbiquitin, and HsUbcH5C, the $eSCF^{FBXL18}$ E3 ligase can be effectively prepared with the fusion protein Flag-eSCR-myc and the protein FBXL18 through reconstitution and a polyubiquitin chain can be formed; and FIG. 8B shows the preparation of an $eSCF^{CDC4}$ E3 ligase with the fusion protein Flag-eSCR-myc and human-derived CDC4 through in vitro reconstitution, and the experimental results show that, in the presence of HsE1, HsUbiquitin, and HsCDC34, the $eSCF^{CDC4}$ E3 ligase can be effectively prepared with the fusion protein Flag-eSCR-myc and the protein CDC4 through in vitro reconstitution to form a polyubiquitin chain.

Figure 2A:
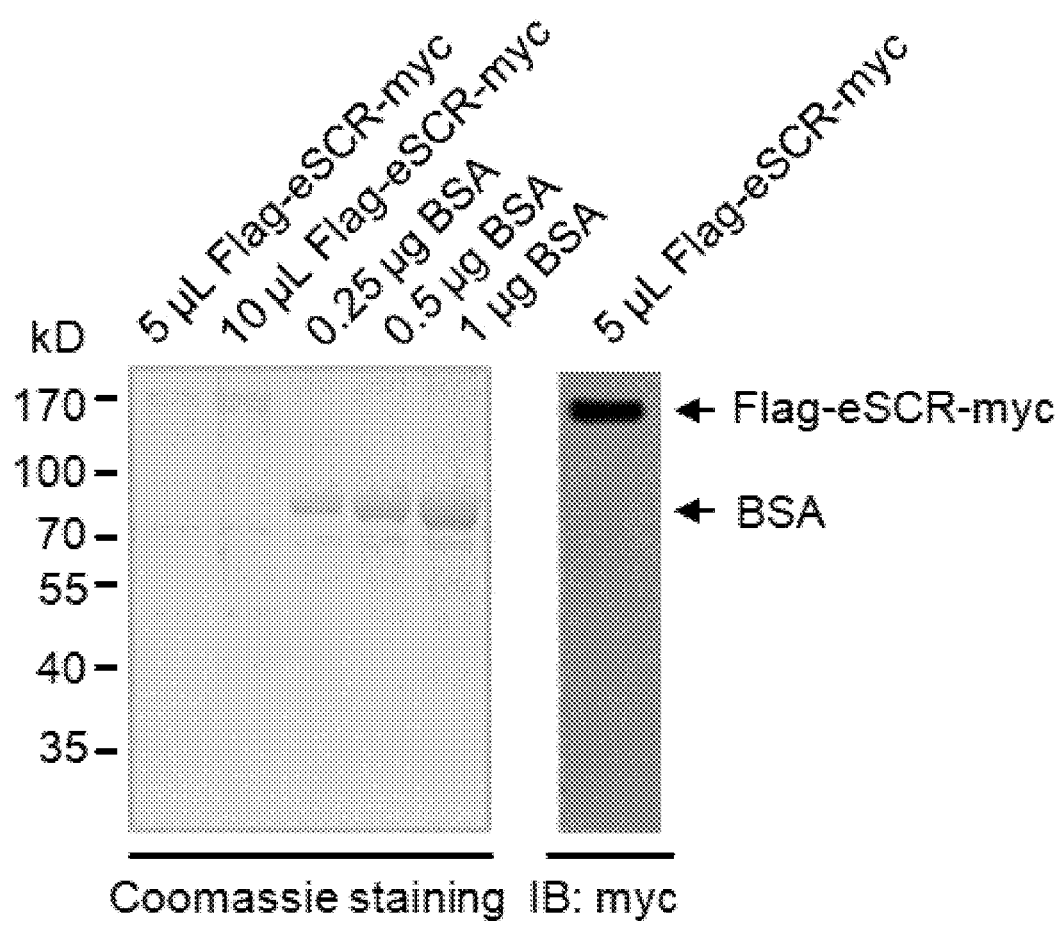
FIGS. 2A-C show the purification and quantification of a fusion protein, the detection of NEDD8 modification, and the detection results of self-ubiquitination activity, where

In the figures, Ub represents ubiquitin.

DETAILED DESCRIPTION OF THE PREFERRED EMBODIMENTS

Unless otherwise specified, the experimental methods described in the following examples are all conventional methods. The methods will be conducted in accordance with the techniques or conditions described in the literature in the art or in accordance with the product specification. All materials, reagents, and instruments used in the following examples may be commercially available, unless otherwise specified. All quantitative tests in the following examples are set to run in triplicate, and the results are averaged. In the following examples, unless otherwise specified, the first nucleotide of each nucleotide sequence in the sequence listing is a 5'-terminus nucleotide of the corresponding DNA/RNA, and the last nucleotide is a 3'-terminus nucleotide of the corresponding DNA/RNA.

50 mM Tris-HCl buffer (pH 7.4): Tris is dissolved in water, and a pH is adjusted with HCl to 7.4, where a concentration of Tris is 50 mM.

Example 1 Preparation of an *Oryza sativa* L.-Derived $eSCF^{D3}$ E3 Ligase with a Fusion Protein Flag-eSCR-Myc Through In Vitro Reconstitution, and a Use of the *Oryza sativa* L.-Derived $eSCF^{D3}$ E3 Ligase In this example, in the presence of OsE1, OsUbiquitin, and OsUBC14, a fusion protein eSCR and a protein D3 were used to prepare an *Oryza sativa* L.-derived multisubunit SCF E3 ligase through in vitro reconstitution, and specific steps were as follows:

In this example, in order to simplify an in vitro active reconstitution system for a multisubunit $SCF^{D3}$ E3 ligase, the three proteins SKP1, Cullin1, and RBX1 were fused in tandem to obtain a fusion protein Flag-SKP1-Cullin1-RBX1-myc (Flag-eSCR-myc), and a schematic diagram and an amino acid sequence of the fusion protein were shown in FIGS. 1A-B, respectively.

An active fusion protein eSCR was prepared as follows:
1.1 Preparation of a Recombinant Vector A Flag-SKP1-Cullin1-RBX1-myc-expressing vector was constructed with a pFastBac Dual vector (Thermofisher, catalog No.: 10712024), and a nucleotide sequence for Flag-SKP1-Cullin1-RBX1-myc was synthesized by Beijing Shengyuan Kemeng Gene Biotechnology Co., Ltd.

With a synthesized Flag-SKP1-Cullin1-RBX1-myc gene fragment as a template, a plasmid was constructed using primers PHSCRFLAGF and PHSCRMYCR (Table 2), and a corresponding promoter was a PH promoter. Specifically, a DNA fragment between EcoRI and SpeI endonuclease recognition sequences of the pFastBac Dual vector was substituted with the eSCR fusion gene from position 1 to position 3219 of SEQ ID NO: 1 in the sequence listing to obtain a vector Flag-SKP1-Cullin1-RBX1-myc, which could express the fusion protein Flag-eSCR-myc with a sequence from position 1 to position 1072 of SEQ ID NO: 2. The obtained recombinant vector was denoted as pFastBac Dual-pPH:Flag-SKP1-Cullin1-RBX1-myc.

TABLE 2

Sequence Information of Primers

| Primer name | Sequence (5'-3') |
|---|---|
| PHSCRFLAGF | TTTGAATTCATGGACTACAAAGACGATGACGACAAGATGGCGGCCGAGGCGGAG (SEQ ID NO: 8) |
| PHSCRMYCR | TTTACTAGTCTACAGATCCTCTTCTGAGATGAGTTTTTGTTCGTGCCCATATTT CTGAAA (SEQ ID NO: 9) |
| CUL1K688AF | GCATCAATTGTGCGTATTATG GCG AGTCGCAAAGTATTGGGTCATC (SEQ ID NO: 10) |
| CUL1K688AR | GATGACCCAATACTTTGCGACTCGCCATAATACGCACAATTGATGC (SEQ ID NO: 11) |
| M13F | GTTTTCCCAGTCACGAC (SEQ ID NO: 12) |
| M13R | CAGGAAACAGCTATGAC (SEQ ID NO: 13) |
| GWOSUBF | GGGGACAAGTTTGTACAAAAAAGCAGGCTTTATGCAGATCTTTGTGAAGACAT (SEQ ID NO: 14) |
| GWOSUBR | GGGGACCACTTTGTACAAGAAAGCTGGGTTTTAGCCACCACGGAGGCGGAGG (SEQ ID NO: 15) |
| GWOSUBC14F | GGGGACAAGTTTGTACAAAAAAGCAGGCTTTATGGCGTCAAAGAGGATACAGAA GGAG (SEQ ID NO: 16) |
| GWOSUBC14R | GGGGACCACTTTGTACAAGAAAGCTGGGTTCTACATGGCGTACCTCTGAGTCCA G (SEQ ID NO: 17) |
| GWOSUBC18F | GGGGACAAGTTTGTACAAAAAAGCAGGCTTTATGGCAAGCAAAAGGATTCAGAA GG (SEQ ID NO:18) |
| GWOSUBC18R | GGGGACCACTTTGTACAAGAAAGCTGGGTTCTAACCCATTGCGTATTTCTGGGT C (SEQ ID NO: 19) |
| GWOSE1F | GGGGACAAGTTTGTACAAAAAAGCAGGCTTTATGCTTCCGACGAAGAGAGCGAA CG (SEQ ID NO: 20) |
| GWOSE1R | GGGGACCACTTTGTACAAGAAAGCTGGGTTCTACCGGAAGTAAATGGAGATGAG A (SEQ ID NO: 21) |
| GWD14F | GGGGACAAGTTTGTACAAAAAAGCAGGCTTTATGCTGCGATCGACGCATCCGCC G (SEQ ID NO: 22) |
| GWD14R | GGGGACCACTTTGTACAAGAAAGCTGGGTTTTAGTACCGGGCGAGAGCGCGGCG (SEQ ID NO: 23) |
| GWD3F | GGGGACAAGTTTGTACAAAAAAGCAGGCTTTATGGCGGAAGAGGAGGAGGTGGA GG (SEQ ID NO: 24) |
| GWD3R | GGGGACCACTTTGTACAAGAAAGCTGGGTTCTAATCATCAATTTGCCGGCTGTT C (SEQ ID NO: 25) |
| PHD3FF | TTTGGATCC ATGGCGGAAGAGGAGGAG (SEQ ID NO: 26) |
| PHD3FR | TTTGAATTCCTACTTGTCGTCATCGTCTTTGTAGTCATCATCAATTTGCCGGCT G (SEQ ID NO: 27) |

TABLE 2-continued

Sequence Information of Primers

| Primer name | Sequence (5'-3') |
|---|---|
| PHCUL1FF | TTTGAATTC ATGGCGACCCACGAGCGGA (SEQ ID NO: 28) |
| PHCUL1FR | TTTACTAGTTCACTTGTCGTCATCGTCTTTGTAGTCAGCCAAGTATCTGTACACA (SEQ ID NO: 29) |
| GWSKP1F | GGGGACAAGTTTGTACAAAAAAGCAGGCTTTATGGCGGCCGAGGCGGAGACGAAGGCGATGATCA (SEQ ID NO: 30) |
| GWSKP1R | GGGGACCACTTTGTACAAGAAAGCTGGGTTTCATTCGAAGGCCCACTGGTTCTCCCTCCTCAC (SEQ ID NO: 31) |
| P10SKP1F | TTTGCTAGC ATGGCGGCCGAGGCGGAG (SEQ ID NO: 32) |
| P10SKP1R | TTTGGTACCTCA TTCGAAGGCCCACTGGT (SEQ ID NO: 33) |
| GWRBX1F | GGGGACAAGTTTGTACAAAAAAGCAGGCTTTATGTCGGCCATGGAGACCGACATCAAC (SEQ ID NO: 34) |
| GWRBX1R | GGGGACCACTTTGTACAAGAAAGCTGGGTTCTAGTGCCCATATTTCTGAAATTCC (SEQ ID NO: 35) |
| P10RBX1F | TTTGCTAGC ATGTCGGCCATGGAGACCGA (SEQ ID NO: 36) |
| P10RBX1R | TTTGGTACCCTA GTGCCCATATTTCTGAAA (SEQ ID NO: 37) |
| GWGID2F | GGGGACAAGTTTGTACAAAAAAGCAGGCTTTATGAAGTTCCGCTCTGATTCGTC (SEQ ID NO: 38) |
| GWGID2R | GGGGACCACTTTGTACAAGAAAGCTGGGTTCTACCCGCATTGGCCCCCTCCATTC (SEQ ID NO: 39) |
| PHGID2FF | TTTGAATTCATGAAGTTCCGCTCTGATTCGTCAG (SEQ ID NO: 40) |
| PHGID2FR | TTTTCTAGATCACTTGTCGTCATCGTCTTTGTAGTCCCCGCATTGGCCCCCTCCATTCTTATC (SEQ ID NO: 41) |
| PHD53INF | CATCGGGCGCGGATCCATGCCCACTCCGGTGGCCGCCGCG (SEQ ID NO: 42) |
| PHD53INHAR | GTAGGCCTTTGAATTCTCAAGCGTAATCTGGAACATCGTATGGGTAACAATCTAGAATTATTCTTGGC (SEQ ID NO: 43) |
| PHHsSic1F | CGACGAGCTCACTAGTATGGACGGGACTATTAAGGAGGCT (SEQ ID NO: 44) |
| PHHsSic1HAR | GACTGCAGGCTCTAGATCAAGCGTAATCTGGAACATCGTATGGGTAGTAGTAGCTGCCTAAGTGTGAAGG (SEQ ID NO: 45) |

In SEQ ID NO: 1, a sequence from position i to position 27 was a DNA sequence of Flag, a sequence from position 28 to position 552 was a DNA sequence of SKP1, a sequence from position 565 to position 2796 was a DNA sequence of Cullin1, a sequence from position 2809 to position 3186 was a DNA sequence of RBX1, and a sequence from position 3187 to position 3219 was a DNA sequence of myc; and in SEQ ID NO: 2, a sequence from position 1 to position 9 was an amino acid sequence of Flag, a sequence from position 10 to position 184 was an amino acid sequence of SKP1, a sequence from position 189 to position 932 was an amino acid sequence of Cullin1, a sequence from position 937 to position 1062 was an amino acid sequence of RBX1, and a sequence from position 1063 to position 1072 was an amino acid sequence of myc. In addition, in order to obtain a functional fusion protein eSCR, linker sequences were added among the protein SKP1, protein Cullin1, and protein RBX1 to ensure the effective interaction among the proteins. In SEQ ID NO: 1, a sequence from position 553 to position 564 and a sequence from position 2797 to position 2808 were DNA sequences encoding linkers; and in SEQ ID NO: 2, a sequence from position 185 to position 188 and a sequence from position 933 to position 936 were amino acid sequences of the linkers.

1.2 Expression of the Fusion Protein Flag-eSCR-Myc

Cultivation conditions for adherent growth of Sf9 insect cells (Novagen, catalog No: 71104-1ML): static cultivation at 26° C. to 28° C.; and cultivation conditions for suspended growth of Sf9 insect cells: suspended cultivation at 26° C. to 28° C. and a low rotational speed (generally 130 rpm to 150 rpm). The pFastBac Dual-pPH:Flag-SKP1-Cullin1-RBX1-myc plasmid was transformed into a Escherichia coli (E. coli) strain DH10Bac, blue-white screening was conducted, and white-spot signal clones were picked and cultivated under shaking; and Bacmid DNA was extracted and identified by PCR with M13F and M13R primers (Table 2) for later use (main operations could be found in the Operation Guide for Bac-to-Bac BaculovirusExpression System of Invitrogen).

Sf9 insect cells growing adherently were transfected with Bacmid DNA expressing the Flag-SKP1-Cullin1-RBX1-myc (abbreviated as Flag-eSCR-myc) fusion protein according to instructions of the Cellfectin II Reagent (Invitrogen, catalog No.: 10362-100) to prepare a P1 insect baculovirus, and 72 h after the cell transfection, a P1 virus was collected. The P1 insect baculovirus was used to infect Sf9 insect cells growing adherently to obtain a P2 insect baculovirus. P3 and P4 insect baculoviruses were acquired in the same way (main operations could be found in the Operation Guide for Bac-to-Bac BaculovirusExpression System of Invitrogen).

An active Flag-eSCR-myc fusion protein was acquired by an insect baculovirus expression system: Sf9 insect cells in suspended growth were infected with the P4 insect baculovirus (a growth density of virus-infected cells was generally $2 \times 10^6$/mL) to allow the expression of a target protein, and generally, 48 h after the viral infection, the insect cells were collected through centrifugation for protein purification.

1.3 Purification of the Fusion Protein Flag-eSCR-Myc

Sf9 insect cells infected with the P4 insect baculovirus obtained in step 1.2 were resuspended with a pre-cooled protein-extracting solution I (formula: 50 mM Tris-HCl (pH 7.5), 100 mM NaCl, 10 mM NaF, 2 mM EDTA (pH 8.0), 10% (v/v, volume percentage) glycerol, 0.5% (v/v, volume percentage) Nonidet P-40, and ingredients added before use: 1 mM PMSF and 1 mM DTT), then disrupted by a high-pressure cell disruptor (JNBIO, model: JN-3000Plus), and then centrifuged at 4° C. and 15,000 g for 20 min, and a resulting protein supernatant was collected.

Flag-eSCR-myc was subjected to affinity purification with Anti-Flag M2 affinity gel (Sigma, catalog No.: A2220-5ML) according to instructions; a Flag-eSCR-myc protein obtained after the affinity purification was further purified with an anion-exchange column CaptoHiRes Q5/50 (GE Healthcare, catalog No.: 29-2758-78), and fractions with high purity and concentration for the Flag-eSCR-myc protein were combined, subjected to buffer exchange with a corresponding ultrafiltration (UF) tube (Millipore, catalog No.: UFC503096), and placed in a Nonidet P-40-free protein-extracting solution I (formula: 50 mM Tris-HCl (pH 7.5), 100 mM NaCl, 10 mM NaF, 2 mM EDTA (pH 8.0), 10% (v/v, volume percentage) glycerol, and ingredients added before use: 1 mM PMSF and 1 mM DTT); and a resulting solution of the fusion protein Flag-eSCR-myc was then dispensed and cryopreserved at −80° C. for later use. The purified fusion protein Flag-eSCR-myc was tested and quantified through CBB staining and WB analysis (FIG. 2A). An antibody used for WB analysis was an anti-myc antibody (Cell Signaling Technology, catalog No.: 2276).

Figure 2B:
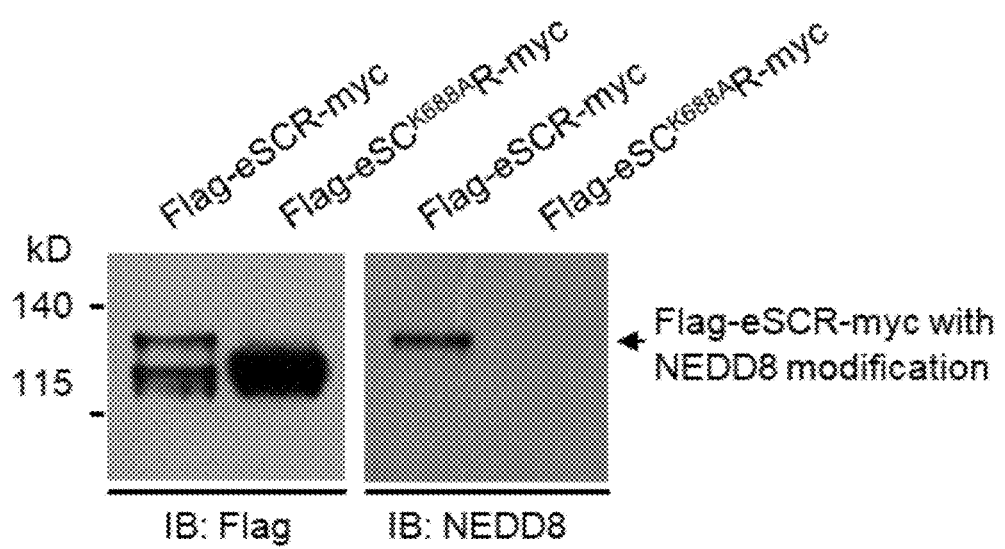

1.4 Verification of Whether the Fusion Protein Flag-eSCR-Myc has Biological Activity The NEDD8 modification on the Cullin1 protein is essential for the biological activity of the Cullin1 protein, and the NEDD8 modification occurs at the Lysine 688 (K688) site of the Cullin1 protein in rice. Therefore, to determine the biological activity of the obtained fusion protein, it is necessary to detect whether the Cullin1 protein in the fusion protein has NEDD8 modification. WB analysis results showed that the purified fusion protein Flag-eSCR-myc obtained in step 1.3 had NEDD8 modification, while the fusion protein Flag-SC$^{K688A}$R-myc did not have an NEDD8 modification signal (In FIG. 2B), indicating that the fusion protein Flag-eSCR-myc was biologically active. Antibodies used for WB analysis were an anti-Flag antibody (Sigma, catalog No.: A8592) and an anti-NEDD8 antibody (Cell signaling technology, catalog No.: 2745).

The fusion protein Flag-SC$^{K688A}$R-myc was prepared through the following steps:

With pFastBac Dual-pPH:Flag-SKP1-Cullin1-RBX1-myc as a template, CUL1K688AF and CUL1K688AR primers (Table 2) and QuikChange Site-Directed Mutagenesis Kit (Stratagene, catalog No.: 200518) were used to mutate a nucleotide for encoding the Lysine 688 site to obtain a recombinant vector pFastBac Dual-pPH:Flag-SKP1-Cullin1K$^{688A}$_RBX1-myc for encoding the fusion protein Flag-SKP1-Cullin1$^{K688A}$_RBX1-myc; and then the fusion protein Flag-SKP1-Cullin1$^{K688A}$_RBX1-myc was subjected to expression, purification, and detection according to step 1.2 and step 1.3. Compared with the WT fusion protein Flag-eSCR-myc, an amino acid at position 688 (namely, position 876 of SEQ ID NO: 2) of Cullin1 in Flag-eSC$^{611}$aR-myc was mutated from lysine to alanine, and there was no NEDD8 modification on the Flag-SC$^{K688A}$R-myc (In FIG. 2B). Experimental results showed that the fusion protein Flag-eSCR-myc used in this experiment was biologically active.

1.5 Verification of Whether the Fusion Protein Flag-eSCR-Myc has Self-Ubiquitination Activity in an In Vitro Ubiquitination Modification System A self-ubiquitination reaction system was obtained by adding MgCl$_2$ (Sigma, catalog No.: M2670), DTT (Sigma, catalog No.: D0632), ATP (Sigma, catalog No.: A7699), His-OsE1, His-OsUBC14, His-OsUbiquitin, and the Flag-eSCR-myc obtained in step 1.3 to 50 mM Tris-HCl buffer (pH 7.4), a reaction system usually had a volume of 30 L, and a content of each component in the system was as follows: MgCl$_2$: 10 mM, DTT: 2 mM, ATP: 5 mM, His-OsE1: 50 ng, His-OsUBC14: 200 ng, His-OsUbiquitin: 5 g, and the Flag-eSCR-myc obtained in step 1.3: 0.8 g. A system without Flag-eSCR-myc was adopted as a negative control.

The reaction system was subjected to a reaction at 28° C. for 2 h. After the reaction was completed, WB analysis was conducted with an anti-Ubiquitin antibody (a product of Cell Signaling Technology).

Figure 2C:
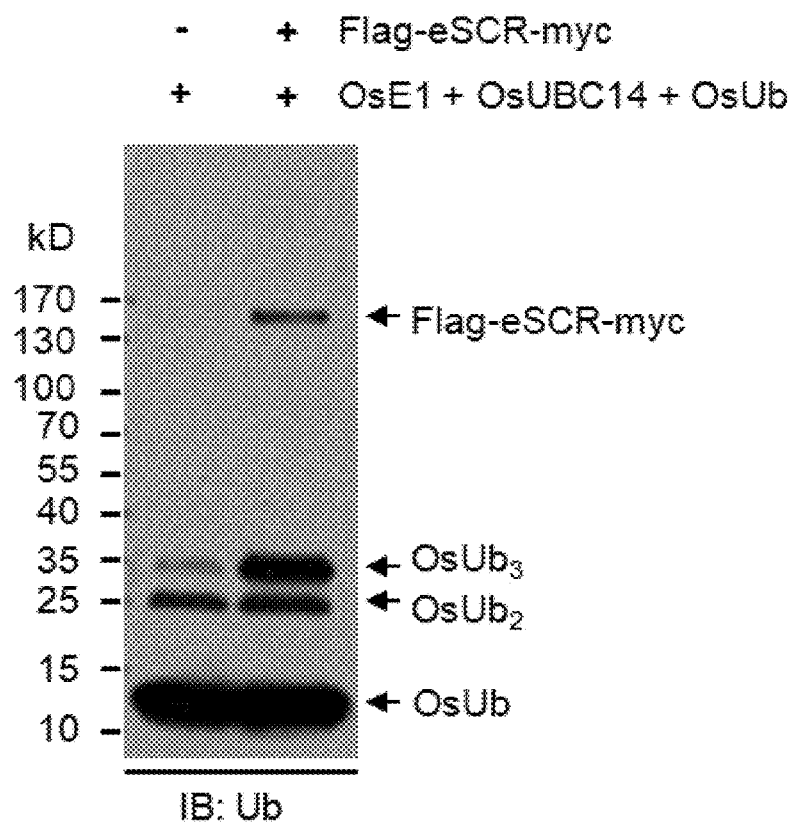

Experimental results showed that the fusion protein Flag-eSCR-myc had no self-ubiquitination activity in the in vitro reconstitution system (In FIG. 2C).

The His-OsE1 protein, His-OsUBC14 protein, and His-OsUbiquitin protein were prepared as follows:

a1) With cDNA of a stem base of an *Oryza sativa* L. Nipponbare seedling as a template, GWOsE1F and GWOsE1R primers, GWOsUBC14F and GWOsUBC14R primers, and GWOSUBF and GWOSUBR primers (Table 2) were used to acquire an OsE1 gene-containing DNA fragment, an OsUBC14 gene-containing DNA fragment, and an OsUb gene-containing DNA fragment through PCR amplification, respectively.

a2) The OsE1, OsUBC14, and OsUb gene fragments each were homologously recombined to an intermediate vector pDONR221 (Invitrogen, catalog No.: 12535-019) using GatewayBP clonase (Invitrogen, catalog No.: P/N56481) to obtain plasmids pDONR221-OsE1, pDONR221-OsUBC14, and pDONR221-OsUb, respectively.

a3) A gene fragment on the plasmid pDONR221-OsE1 was recombined to the terminal protein expression vector pET-55-DEST (Novagen, catalog No.: 71846, which had a His tag at a C-terminus and a Strep-tag at an N-terminus) using Gateway LR clonase (Invitrogen, catalog No.: P/N56484); gene fragments on pDONR221-OsUBC14 and pDONR221-OsUb each were homologously recombined to the terminal protein expression vector pET-61-DEST (Novagen, catalog No.: 71852, which had a His tag at an N-terminus) by the same method; and sequencing was conducted for confirmation to obtain plasmids pET-55-DEST-OsE1, pET-61-DEST-OsUBC14, and pET-61-DEST-OsUb for the overexpression of the protein OsE1, protein OsUBC14, and protein OsUb, respectively. Genes encoding the protein OsE1, protein OsUBC14, and protein OsUb had accession numbers of LOC_Os03g18380 (update date: 2021.7.1), LOC_Os01g46926 (update date: 2021.7.1), and LOC_Os05g42424 (update date: 2021.7.1) (rice.plantbiology.msu.edu/), respectively.

a4) The plasmids pET-55-DEST-OsE1, pET-61-DEST-OsUBC14, and pET-61-DEST-OsUb each were transformed into a protein-expressing *E. coli* strain BL21 (DE3); monoclones were picked, inoculated into 10 mL of an LB liquid medium (formula: 10 g/L Tryptone, 5 g/L yeast extract, and 10 g/L NaCl), and cultivated overnight at 37° C. for bacterial activation; an activated bacterial culture was subjected to expanded cultivation at 37° C. according to a ratio of 1:100 and cultured until $OD_{600}$ was 0.8, then isopropyl-β-D-thiogalacto side (IPTG) was added at a final concentration of 0.3 mM, and the protein expression was induced at 16° C. and 180 rpm generally for 16 h to 20 h; and bacteria were collected through centrifugation to obtain His-OsE1 protein-expressing bacteria, His-OsUBC14 protein-expressing bacteria, and His-OsUb protein-expressing bacteria.

a5) The His-OsE1 protein-expressing bacteria, His-OsUBC14 protein-expressing bacteria, and His-OsUb protein-expressing bacteria each were resuspended with a protein-extracting solution I (formula: 50 mM Tris-HCl (pH 7.5), 100 mM NaCl, 10 mM NaF, 20 mM imidazole, 10% (v/v) Glycerol, 0.5% (v/v) Nonidet P-40, and ingredients added before use: 1 mM PMSF and 1 mM DTT), disrupted with a high-pressure cell disruptor (JNBIO, model: JN-3000Plus), and centrifuged at 4° C. and 15,000 g for 20 min; resulting protein supernatants each were collected and incubated with the Ni Sepharose 6 Fast Flow resin packing (GE Healthcare, catalog No.: 17-5318-01) according to instructions; and after the incubation was completed, resin packings combining the His-OsE1 protein, His-OsUBC14 protein, and His-OsUb protein each were rinsed with a protein-extracting solution II, and then the His-OsE1 protein, His-OsUBC14 protein, and His-OsUb protein each were eluted and collected with 50 mM imidazole, 100 mM imidazole, 250 mM imidazole, and 500 mM imidazole to obtain the His-OsE1 protein, His-OsUBC14 protein, and His-OsUb protein.

1.6 Verification of an Interaction Between the Fusion Protein Flag-eSCR-Myc and the Protein D3

A GST-D3 protein was prepared through the following steps:

b1) With cDNA of a stem base of an *Oryza sativa* L. Nipponbare seedling as a template, GWD3F and GWD3R primers (Table 2) were used to clone a D3 gene fragment to the terminal protein overexpression plasmid pET-60-DEST (Novagen, catalog No.: 71851, which had a GST tag at an N-terminus) according to steps a1) to a3) in 1.5 to obtain a plasmid pET-60-DEST-D3, where a gene encoding the protein D3 had an accession number of LOC_Os06g06050 (update date: 2021.7.1) (rice.plantbiology.msu.edu/). b2) The protein GST-D3 was expressed and purified according to steps a4) and a5) in 1.5, where the protein GST-D3 was purified with a Glutathione Sepharose 4 Fast Flow (GE Healthcare, catalog No.: 17-5132-01) resin packing; bacteria were resuspended with a protein-extracting solution II (formula: 50 mM Tris-HCl (pH 7.5), 100 mM NaCl, 10 mM NaF, 2 mM EDTA (pH 8.0), 10% (v/v) Glycerol, 0.5% (v/v) Nonidet P-40, and ingredients added before use: 1 mM PMSF and 1 mM DTT); and the resulting GST-D3 agarose gel could be used for a GST-D3 pulldown test.

The fusion protein Flag-eSCR-myc obtained from steps 1.1 to 1.3 was taken, the agarose gel including 1 mg of the protein GST-D3 were mixed with 100 L of a Flag-eSCR-myc fusion protein lysate, and a resulting mixture was incubated at 4° C. and 10 rpm for 1 h to 2 h. After the incubation was completed, the mixture was centrifuged at a low speed, a resulting supernatant was removed, and the agarose gel were washed with a protein-extracting solution I (formula: 50 mM Tris-HCl (pH 7.5), 100 mM NaCl, 10 mM NaF, 2 mM EDTA (pH 8.0), 10% (v/v, volume percentage) Glycerol, 0.5% (v/v, volume percentage) Nonidet P-40, and ingredients added before use: 1 mM PMSF and 1 mM DTT) 4 to 5 times. WB analysis was conducted with an anti-myc antibody (Cell Signaling Technology, catalog No.: 2276).

Figure 3:
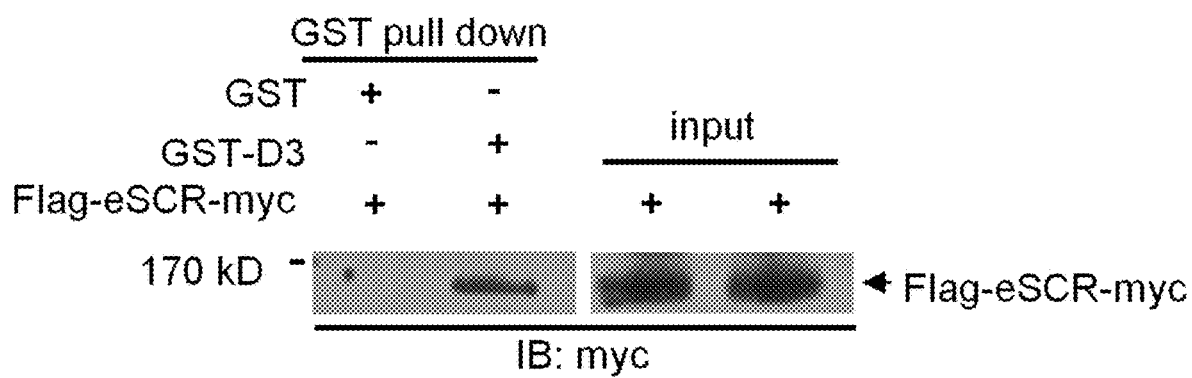
FIG. 3 shows the interaction between the fusion protein eSCR and the protein D3 verified by GST-Pulldown, where the experimental results show that there is an interaction between the fusion protein eSCR and the protein D3; and Flag-eSCR-myc represents Flag-SKP1-Cullin1-RBX1-myc.

The interaction between the fusion protein eSCR and the protein D3 was verified by the GST-D3 Pulldown assay, and results showed that there was an interaction between the fusion protein eSCR and the protein D3 (FIG. 3).

1.7 Preparation of an $eSCF^{D3}$ E3 Ligase with the Fusion Protein Flag-eSCR-Myc Through In Vitro Reconstitution A system for preparing the $eSCF^{D3}$ E3 ligase with the fusion protein Flag-eSCR-myc through in vitro active reconstitution was obtained by adding $MgCl_2$, DTT, ATP, His-OsE1, His-OsUBC14, His-OsUbiquitin, D3-Flag, and the Flag-eSCR-myc obtained in step 1.3 to 50 mM Tris-HCl buffer (pH 7.4), a reaction system usually had a volume of 30 μL, and a content of each component in the reaction system was as follows: $MgCl_2$: 10 mM, DTT: 2 mM, ATP: 5 mM, His-OsE1: 50 ng, His-OsUBC14: 200 ng, His-OsUbiquitin: 5 g, D3-Flag: 0.5 g, and Flag-eSCR-myc: 0.8 g. In order to ensure a consistent start time for parallel reactions, the components were added in the following order during the activity analysis test: His-OsUBC14, His-OsUbiquitin, an $eSCF^{D3}$ complex (including the two components of D3-Flag and Flag-eSCR-myc, where an addition order of the components was not strictly restricted), His-OsE1, and 20×reaction buffer (formula: 1 M Tris (pH 7.4), 200 mM $MgCl_2$, 100 mM ATP, and 40 mM DTT). The three proteins of Cullin1-Flag, His-SKP1, and His-RBX1 each were used as controls instead of Flag-eSCR-myc.

Figure 4:
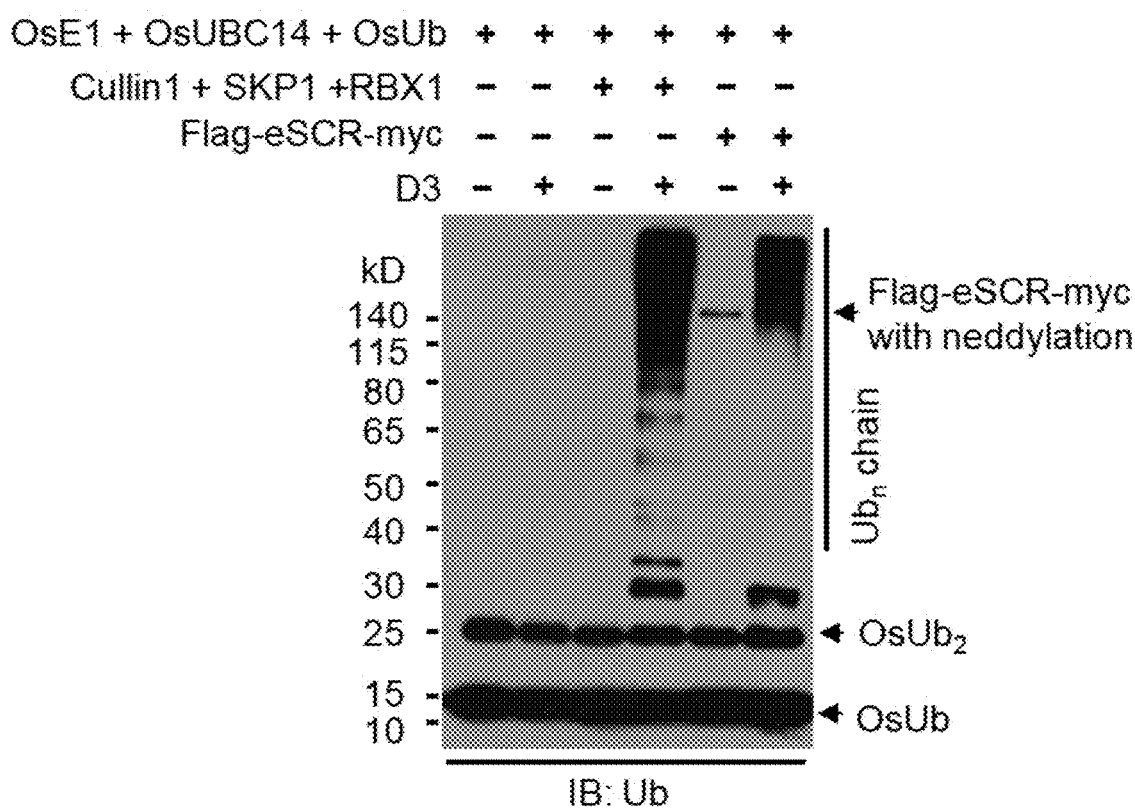
FIG. 4 shows the preparation of a multisubunit $SCF^{D3}$ E3 ligase with the fusion protein Flag-eSCR-myc through in vitro reconstitution, where the experimental results show that, in the presence of OsE1, OsUbiquitin, and OsUBC14, compared with the preparation of wild-type $SCF^{D3}$ E3 ligase (WT $SCF^{D3}$ E3 ligase) through in vitro reconstitution using the SKP1 protein, Cullin1 protein, RBX1 protein, and D3 protein, an engineered $SCF^{D3}$ E3 ligase ($eSCF^{D3}$ E3 ligase) can also be effectively reconstituted using the fusion protein eSCR and the protein D3 to form a polyubiquitin chain.

The in vitro ubiquitination assay sample was subjected to a reaction at 28° C. for 2 h; after the reaction was completed, 6×SDS sample loading buffer was added to terminate the reaction; and an active reaction sample was subjected to sodium dodecyl sulfate-polyacrylamide gel electrophoresis (SDS-PAGE) and WB analysis, then incubated with an anti-Ubiquitin antibody (Cell Signaling Technology, catalog No.: 3936) and an anti-mouse-HRP antibody (GE Health, catalog No.: NA931V) successively, and subjected to development. Experimental results showed that, compared with the WT $SCF^{D3}$ E3 ligase obtained through reconstitution (namely, a ligase obtained through the reconstitution of Cullin1-Flag, His-SKP1, and His-RBX1 with D3-Flag), the $eSCF^{D3}$ E3 ligase obtained through the reconstitution of the fusion protein Flag-eSCR-myc with the protein D3 also has E3 ligase activity (FIG. 4).

The protein D3-Flag and the protein Cullin1-Flag each were prepared through the following steps:

Construction of a plasmid co-expressing the protein Cullin1-Flag and the protein RBX1 and a plasmid co-expressing the protein D3-Flag and the protein SKP1: Because the protein RBX1 could promote the NEDD8 modification of the protein Cullin1 to enhance the activity of the protein Cullin1, the plasmid co-expressing the protein Cullin1-Flag and the protein RBX1 was constructed. Because the protein SKP1 could stabilize the protein F-box, a plasmid co-expressing the protein D3-Flag and the protein SKP1 was constructed.

c1) With cDNA of a stem base of an *Oryza sativa* L. Nipponbare seedling as a template, the P10RBX1F and P10RBX1R primers and the PHCUL1FF and PHCUL1FR primers (Table 2) were used to acquire gene fragments RBX1 and Cullin1-Flag through PCR amplification, respectively; the gene fragment RBX1 and a pFastBac Dual vector (Thermofisher, catalog No.: 10712024) each were subjected to double enzyme digestion with endonucleases KpnI and NheI, and a gene fragment RBX1 and a pFastBac Dual vector obtained after the double enzyme digestion were recovered and then ligated with a Ligation High kit (TOYOBO, catalog No.: LGK-201) to obtain a plasmid pFastBac Dual-pP10:RBX1; and the gene fragment Cullin1-Flag and the pFastBac Dual-pP10:RBX1 plasmid each were subjected to double enzyme digestion with endonucleases EcoRI and SpeI, and a gene fragment Cullin1-Flag and a pFastBac Dual-pP10: RBX1 plasmid obtained after the double enzyme digestion were recovered and then ligated with a Ligation High kit to obtain the plasmid pFastBac Dual-pP10:RBX1-pPH:Cullin1-Flag co-expressing the protein Cullin1-Flag and the protein RBX1. With cDNA of a stem base of an *Oryza sativa* L. Nipponbare seedling as a template, the P10SKP1F and P10SKP1R primers and the PHD3FF and PHD3FR primers (Table 2) were used to acquire gene fragments SKP1 and D3-Flag through PCR amplification; and the same molecular cloning method was used to construct the plasmid pFastBac Dual-pP10:SKP1-pPH:D3-Flag co-expressing the protein D3-Flag and the protein SKP1, where endonucleases KpnI and NheI were used for the double enzyme digestion of the gene fragment SKP1, and endonucleases BamHI and EcoRI were used for the double enzyme digestion of the gene fragment D3-Flag. Genes encoding the protein Cullin1, protein RBX1, protein D3, and protein SKP1 had accession numbers of LOC_Os01g27150 (update date: 2021.7.1), LOC_Os01g01700 (update date: 2021.7.1), LOC_Os06g06050 (update date: 2021.7.1), and LOC_Os09g36830 (update date: 2021.7.1) (rice.plantbiology.msu.edu/).

c2) Preparation and identification of Bacmid DNA: The plasmids pFastBac Dual-pP10: RBX1-pPH:Cullin1-Flag and pFastBac Dual-pP10:SKP1-pPH:D3-Flag each were transformed into an *E. coli* strain DH10Bac, blue-white screening was conducted, and white-spot single clones were picked and cultivated under shaking; and Bacmid DNA was extracted and identified by PCR with M13F and M13R primers for later use (main operations could be found in the Operation Guide for Bac-to-Bac BaculovirusExpression System of Invitrogen).

c3) Preparation of insect baculoviruses expressing the protein Cullin1-Flag and the protein D3-Flag: Cultivation conditions for adherent growth of Sf9 insect cells (Novagen, catalog No.: 71104-1ML) were as follows: static cultivation at 26° C. to 28° C.; and cultivation conditions for suspended growth of Sf9 insect cells were as follows: suspended cultivation at 26° C. to 28° C. and a low rotational speed (generally 130 rpm to 150 rpm). Sf9 insect cells growing adherently were transfected with the Bacmid DNA co-expressing the protein Cullin1-Flag and the protein RBX1 and the Bacmid DNA co-expressing the protein D3-Flag and the protein SKP1 obtained in step c2) according to instructions of the Cellfectin II Reagent (Invitrogen, catalog No.: 10362-100) to prepare P1 insect baculoviruses, and 72 h after the cell transfection, P1 viruses were collected. The P1 insect baculoviruses each were used to infect Sf9 insect cells growing adherently to obtain P2 insect baculoviruses. P3 and P4 insect baculoviruses were acquired in the same way (operations could be found in the Operation Guide for Bac-to-Bac Baculovirus Expression System of Invitrogen).

c4) Acquisition of active proteins Cullin1-Flag and D3-Flag by an insect baculovirus expression system: Suspended Sf9 insect cells were infected with the P4 insect baculovirus (a growth density of virus-infected cells was generally $2 \times 10^6$/mL) to allow the expression of a target protein, and generally, 48 h after the viral infection, the insect cells were collected through centrifugation for protein purification.

c5) The cells were resuspended with a pre-cooled protein-extracting solution I, then disrupted with a high-pressure cell disruptor (JNBIO, model: JN-3000Plus), and then centrifuged at 4° C. and 15,000 g for 20 min, and a resulting protein supernatant was collected.

c6) The protein supernatant was subjected to purification with Anti-Flag M2 affinity gel (Sigma, catalog No.: A2220-5ML) according to instructions; and the protein D3-Flag and the protein Cullin1-Flag each were eluted with a protein eluent (formula: 20 mM Tris-HCl (pH 7.5), 500 ng/mL 3×Flag peptide (Sigma, catalog No.: F4799-25MG), and 10 mM NaCl).

c7) The protein D3-Flag and the protein Cullin1-Flag obtained after the expression and purification in c3) to c6) each were further purified with an anion-exchange column Capto HiRes Q5/50 (GE Healthcare, catalog No.: 29-2758-78), and fraction components obtained after the purification of the anion-exchange column were tested by SDS-PAGE and CBB staining.

c8) According to the CBB staining results in c7), fractions with high purity and high concentration were combined, and a corresponding UF tube (Millipore, catalog No.: UFC503096) was used to replace the protein buffer with a protein-extracting solution I.

c9) The proteins obtained in c8) were tested and quantified by SDS-PAGE and CBB staining, and then the purified proteins D3-Flag and Cullin1-Flag each were dispensed and stored at −80° C. for later use.

The protein His-SKP1 and the protein His-RBX1 each were prepared through the following steps:

d1) With cDNA of a stem base of an *Oryza sativa* L. Nipponbare seedling as a template, the GWSKP1F and GWSKP1R primers and the GWRBX1F and GWSRBX1R primers (Table 2) were used to clone gene fragments SKP1 and RBX1 to the terminal protein overexpression plasmid pET-61-DEST (Novagen, catalog No.: 71852, which had a His tag at an N-terminus) according to steps a1) to a3) to obtain plasmids pET-61-DEST-SKP1 and pET-61-DEST-RBX1, respectively.

d2) The protein His-SKP1 and the protein His-RBX1 each were expressed and purified according to steps a4) and a5), and the purified proteins His-SKP1 and His-RBX1 were dispensed and stored at −80° C. for later use.

1.8 Ubiquitination Analysis of a Protein D53

The ubiquitination of the protein D53 was analyzed with an in vitro reconstitution system for a multisubunit $SCF^{D3}$ E3 ligase, where the in vitro reconstitution system was obtained by adding $MgCl_2$, DTT, ATP, His-OsE1, His-OsUBC14, His-OsUbiquitin, D3-Flag, Flag-eSCR-myc, and D53-HA to 50 mM Tris-HCl buffer (pH 7.4), a reaction system usually had a volume of 30 L, and a content of each component in the reaction system was as follows: $MgCl_2$: 10 mM, DTT: 2 mM, ATP: 5 mM, His-OsE1: 50 ng, His-OsUBC14: 200 ng, His-OsUbiquitin: 5 g, D3-Flag: 0.5 g, Flag-eSCR-myc: 0.8 g, and D53-HA: 100 ng. In order to ensure a consistent start time for parallel reactions, the components were added in the following order during the activity analysis test: His-OsUBC14, His-OsUbiquitin, D53-HA, SCF$^{D3}$ complex (including D3-Flag, Cullin1-Flag, His-SKP1, and His-RBX1 or Flag-eSCR-myc, where an addition order of the components was not strictly restricted), His-OsE1, and 20×reaction buffer (formula: 1 M Tris (pH 7.4), 200 mM MgCl$_2$, 100 mM ATP, and 40 mM DTT).

The in vitro ubiquitination assay sample was conducted at 28° C. for 2 h; after the reaction was completed, 6×SDS sample loading buffer was added to terminate the reaction; and an active reaction sample was subjected to SDS-PAGE and WB analysis, then incubated with an anti-Ubiquitin antibody or an anti-HA antibody (Roche, catalog No.: 11867423001) and an anti-mouse-HRP antibody successively, and subjected to development.

Figure 5A:
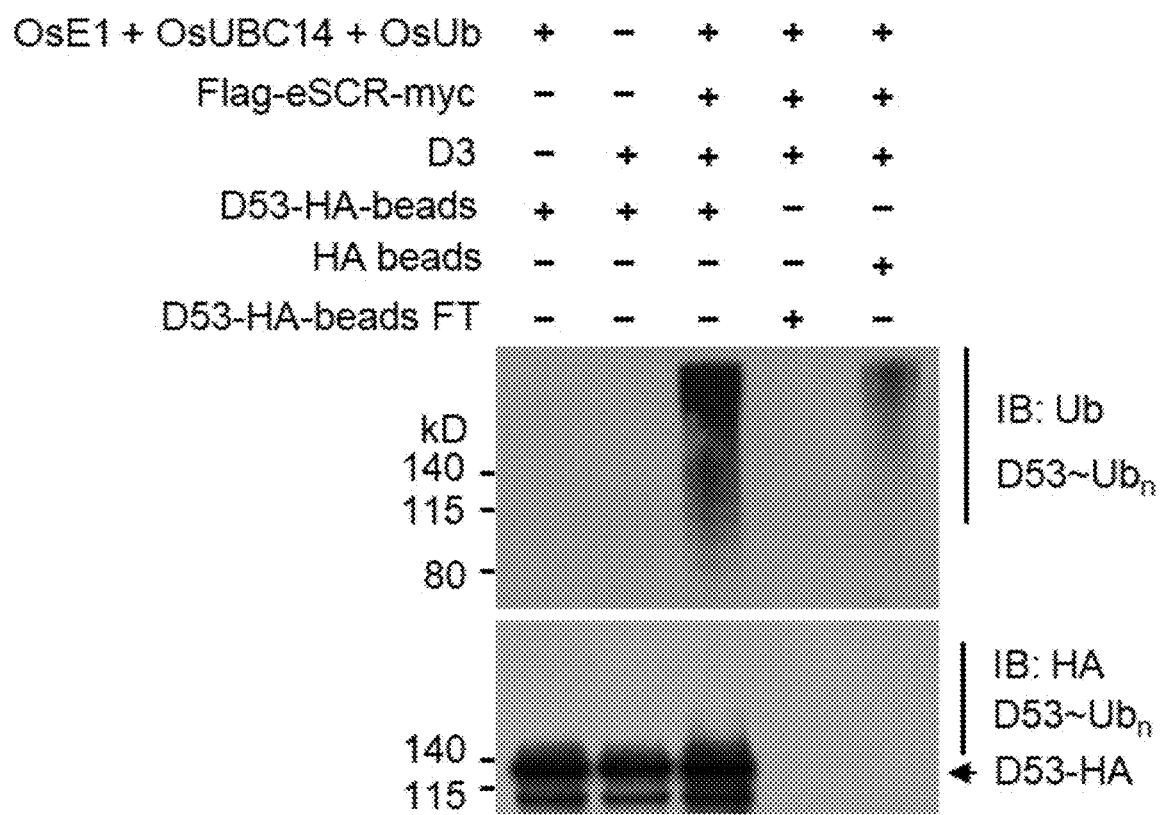
FIGS. 5A-B shows the experimental results of D53's ubiquitination by the $eSCF^{D3}$ E3 ligase obtained through in vitro reconstitution using a fusion protein Flag-eSCR-myc and a protein D3, where
Figure 5B:
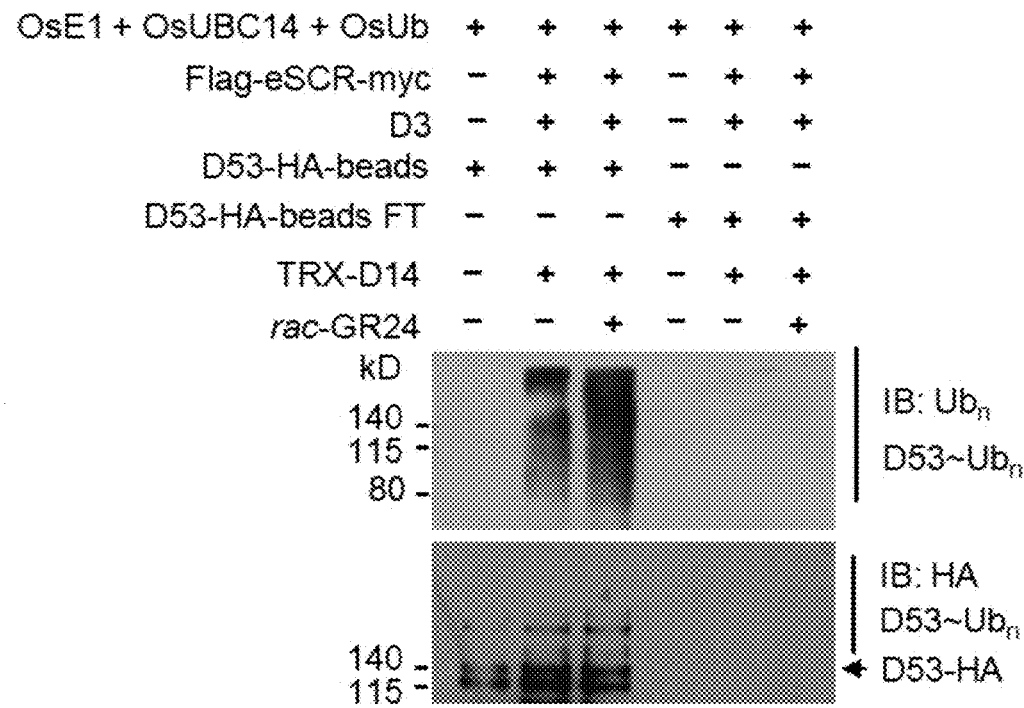

Experimental results showed that both the WT SCF$^{D3}$ ligase obtained through in vitro reconstitution and the SCF$^{D3}$ E3 ligase obtained through reconstitution with the fusion protein Flag-eSCR-myc could ubiquitinate the protein D53 (In FIG. 5A); and in the presence of the strigolactone receptor protein D14 (a concentration of the protein TRX-D14 in the system was 0.5 g/30 L) and strigolactone analog rac-GR24 (Chiralix, catalog No.: CX23880, where a concentration of rac-GR24 in the system was 56 M), the ubiquitination of the protein D53 by the SCF$^{D3}$ E3 ligase obtained through in vitro reconstitution was enhanced (In FIG. 5B). The above results also showed that the SCF$^{D3}$ E3 ligase obtained through reconstitution with the fusion protein eSCR had the same biological activity as the WT SCF$^{D3}$ E3 ligase obtained through reconstitution, could effectively catalyze the ubiquitination of the substrate protein D53, and had high sensitivity for studying strigolactone signal transduction.

The protein D53-HA was prepared through the following steps:

e1) With cDNA of a stem base of an *Oryza sativa* L. Nipponbare seedling as a template, the PHD53INF and PHD53INHAR primers (Table 2) were used to clone the gene fragment D53-HA with the tag encoding the HA fusion protein to a pFast BacDual vector according to the step c1) to obtain a plasmid pFastBac Dual-pPH:D53-HA, where endonucleases BamHI and EcoRI were used to construct the plasmid; and a gene encoding the protein D53 had an accession number of LOC_Os11g01330 (update date: 2021.7.1) (rice.plantbiology.msu.edu/).

e2) The protein D53-HA was expressed with an insect baculovirus expression system according to steps c2) to c4) and purified according to steps c5) to c9), where anti-HA agarose (Sigma, catalog No.: A2095) was used for the purification of the protein D53-HA and 500 ng/mL 1×HA peptide (Sigma, catalog No.: 12149) was used for the elution of the protein D53-HA; and the purified protein D53-HA was finally dispensed and stored at −80° C. for later use.

The protein TRX-D14 was prepared through the following steps:

e1) With cDNA of a stem base of an *Oryza sativa* L. Nipponbare seedling as a template, GWD14F and GWD14R primers (Table 2) were used to clone a D14 gene fragment to a terminal protein overexpression plasmid pET-59-DEST (Novagen, catalog No.: 71850, which had tags His and TRX at an N-terminus) according to steps a1) to a3) to obtain a plasmid pET-59-DEST-D14, where a gene encoding the protein D14 had an accession number of LOC_Os01g10620 (update date: 2021.7.1) (rice.plantbiology.msu.edu/).

e2) The protein His-TRX-D14 (abbreviated as protein TRX-D14) was expressed and purified according to steps a4) and a5), and the purified protein TRX-D14 was dispensed and stored at −80° C. for later use.

Example 2 Preparation of an *Oryza sativa* L.-Derived SCF$^{GID2}$ E3 Ligase with a Fusion Protein Flag-eSCR-Myc Through In Vitro Reconstitution 2.1 Verification of an Interaction Between the Fusion Protein Flag-eSCR-Myc and the F-Box Protein GID2 Through GST-GID2 Pulldown A protein GST-GID2 was prepared through the following steps:

f1) With cDNA of a stem base of an *Oryza sativa* L. Nipponbare seedling as a template, GWGID2F and GWGID2R primers (Table 2) were used to clone a gene fragment GID2 to a terminal protein overexpression plasmid pET-60-DEST (Novagen, catalog No.: 71851, which had a GST tag at an N-terminus) according to steps a1) to a3) to obtain a plasmid pET-60-DEST-GID2, where a gene encoding the protein GID2 had an accession number of AB100246.1 (update date: 2021.7.1) (rice.plantbiology.msu.edu/).

f2) The protein GST-GID2 was purified according to the step b2), and the obtained GST-GID2 agarose gel could be used in a GST-GID2 pulldown assay.

The fusion protein Flag-eSCR-myc obtained from steps 1.1 to 1.3 in Example 1 was taken, agarose gel including 1 mg of the protein GST-GID2 was mixed with 100 L of a Flag-eSCR-myc fusion protein lysate, and a resulting mixture was incubated at 4° C. and 10 rpm for 1 h to 2 h. After the incubation was completed, the mixture was centrifuged at a low speed, a resulting supernatant was removed, and the agarose gel were washed with a protein-extracting solution I (formula: 50 mM Tris-HCl (pH 7.5), 100 mM NaCl, 10 mM NaF, 2 mM EDTA (pH 8.0), 10% (v/v, volume percentage) Glycerol, 0.5% (v/v, volume percentage) Nonidet P-40, and ingredients added before use: 1 mM PMSF and 1 mM DTT) 4 to 5 times. WB analysis was conducted with an anti-myc antibody (Cell Signaling Technology, catalog No.: 2276).

Figure 6:
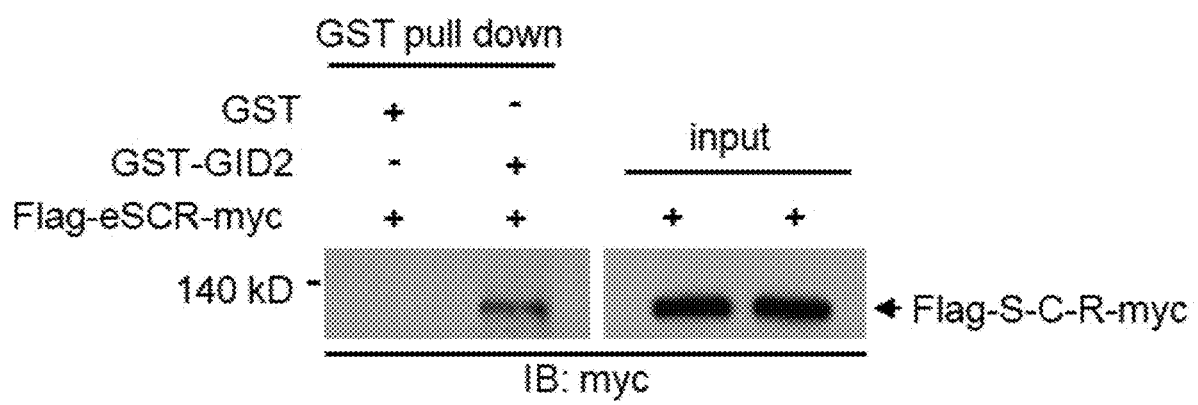
FIG. 6 shows the interaction between the fusion protein Flag-eSCR-myc and the protein GID2 verified by GST-Pulldown, where the experimental results show that there is an interaction between the fusion protein Flag-eSCR-myc and the protein GID2.

The experimental results showed that there was an interaction between the fusion protein eSCR and the protein GID2 (FIG. 6).

2.2 Preparation of an *Oryza sativa* L.-Derived eSCF$^{GID2}$ E3 Ligase with the Fusion Protein Flag-eSCR-Myc Through In Vitro Reconstitution A system for preparing the *Oryza sativa* L.-derived eSCF$^{GID2}$ E3 ligase with the fusion protein Flag-eSCR-myc through in vitro reconstitution was obtained by adding MgCl$_2$, DTT, ATP, His-OsE1, His-OsUBC18, His-OsUbiquitin, GID2-Flag, and the Flag-eSCR-myc obtained in Example 1 to 50 mM Tris-HCl buffer (pH 7.4), a reaction system usually had a volume of 30 μL, and a content of each component in the reaction system was as follows: MgCl$_2$: 10 mM, DTT: 2 mM, ATP: 5 mM, His-OsE1: 50 ng, His-OsUBC18: 200 ng, His-OsUbiquitin: 5 g, GID2-Flag: 0.25 g, and Flag-eSCR-myc: 0.8 g. In order to ensure a consistent start time for parallel reactions, the components were added in the following order during the activity analysis test: His-OsUBC18, His-OsUbiquitin, an SCF$^{GID2}$ complex (including the two components GID2-Flag and Flag-eSCR-myc, where an addition order of the components was not strictly restricted), His-OsE1, and 20×reaction buffer (formula: 1 M Tris (pH 7.4), 200 mM MgCl$_2$, 100 mM ATP, and 40 mM DTT).

The in vitro active reconstitution was conducted at 28° C. for 2 h; after the reaction was completed, 6×SDS sample loading buffer was added to terminate the reaction; and an active reaction sample was subjected to SDS-PAGE and WB analysis, then incubated with an anti-Ubiquitin antibody and an anti-mouse-HRP antibody successively, and subjected to development.

Figure 7:
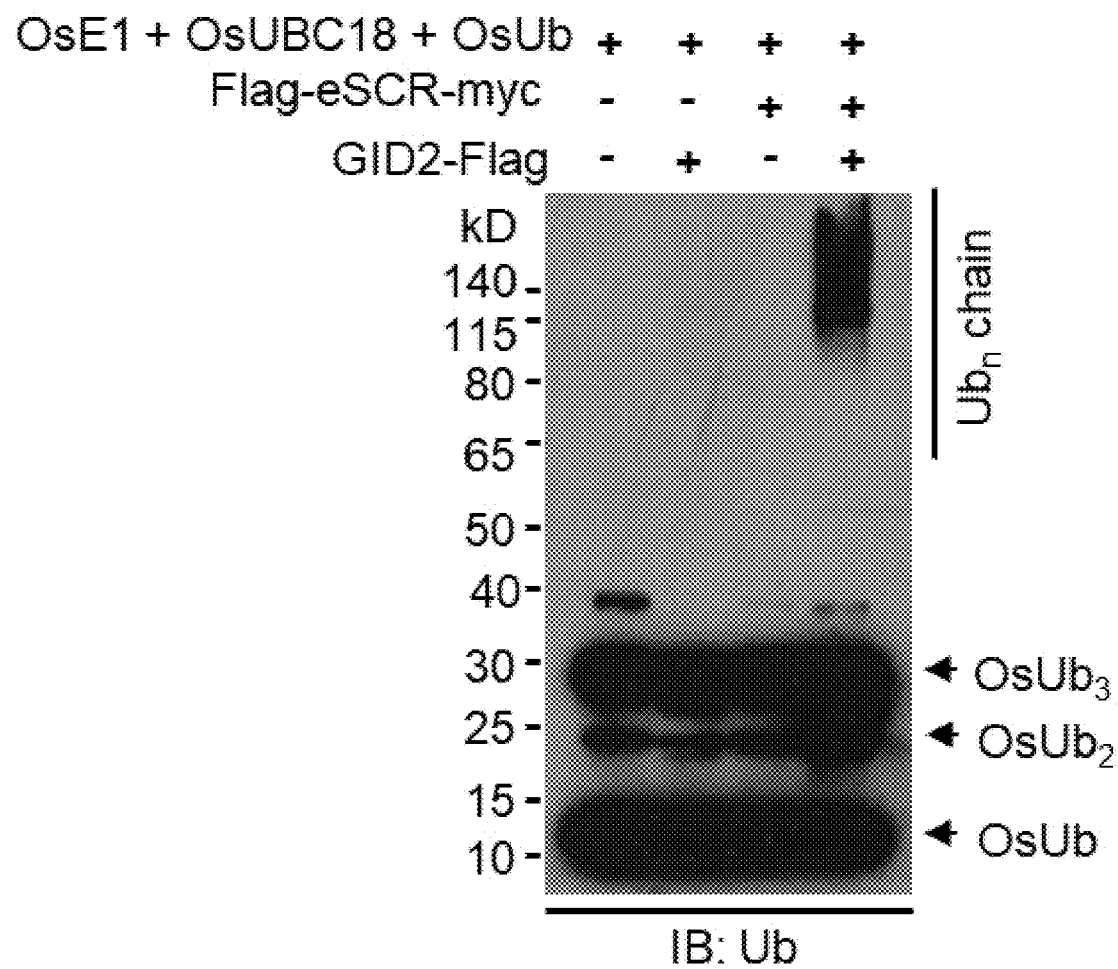
FIG. 7 shows the preparation of a multisubunit $eSCF^{GID2}$ E3 ligase with the fusion protein Flag-eSCR-myc through in vitro reconstitution, where the experimental results show that, in the presence of OsE1, OsUbiquitin, and OsUBC18, the $eSCF^{GID2}$ E3 ligase can be effectively prepared with the fusion protein Flag-eSCR-myc and the protein GID2 through in vitro reconstitution and a polyubiquitin chain can be formed.

The experimental results showed that, in the presence of OsE1, OsUbiquitin, and OsUBC18, the SCF$^{GID2}$ E3 ligase could be effectively prepared with the fusion protein Flag-eSCR-myc and the protein GID2 through active reconstitution to form a polyubiquitin chain (FIG. 7).

The protein GID2-Flag was prepared through the following steps:

g1) With cDNA of a stem base of an *Oryza sativa* L. Nipponbare seedling as a template, the PHGID2FF and PHGID2FR primers (Table 2) were used to clone the gene fragment GID2-Flag with the tag encoding the Flag fusion protein to a pFastBac Dual vector according to the step c1) to obtain a plasmid pFastBac Dual-pPH:GID2-Flag, where endonucleases EcoRI and XbaI were used to construct the plasmid; and a gene encoding the protein GID2 had an accession number of AB100246.1 (update date: 2013.1) (rice.plantbiology.msu.edu/).

g2) The protein GID2-Flag was expressed with an insect baculovirus expression system according to steps c2) to c4) and purified according to steps c5) to c9); and finally, the purified protein GID2-Flag was dispensed and stored at −80° C. for later use.

The protein His-OsUBC18 was prepared through the following steps:

h1) GWOsUBC18F and GWOsUBC18R primers (Table 2) were used to clone a gene fragment OsUBC18 to a terminal protein overexpression plasmid pET-61-DEST (Novagen, catalog No.: 71852, which had a His tag at an N-terminus) according to steps a1) to a3) to obtain a plasmid pET-61-DEST-OsUBC18, where a gene encoding the protein OsUBC18 had an accession number of LOC_Os01g1223 (2021.7.1) (rice.plantbiology.msu.edu/).

h2) The protein His-OsUBC18 was expressed and purified according to steps a4) and a5), and the purified protein His-OsUBC18 was dispensed and stored at −80° C. for later use.

Example 3 Preparation of a Human-Derived eSCF$^{FBXL18}$ E3 Ligase with a Fusion Protein Flag-eSCR-Myc Through In Vitro Reconstitution A system for preparing the human-derived eSCF$^{FBXL18}$ E3 ligase with the fusion protein Flag-eSCR-myc through in vitro reconstitution was obtained by adding MgCl$_2$, DTT, ATP, HsE1 (BostonBiochem, catalog No.: E-305), HsUbcH5C (Boston Biochem, catalog No.: E2-627), HsUbiquitin (Boston Biochem, catalog No.: U-110), HsFBXL18 (Abnova, catalog No.: H00080028-P01), and the Flag-eSCR-myc in Example 1 to 50 mM Tris-HCl buffer (pH 7.4), a reaction system usually had a volume of 30 L, and a content of each component in the reaction system was as follows: MgCl$_2$: 10 mM, DTT: 2 mM, ATP: 5 mM, HsE1: 50 ng, HsUbcH5C: 200 ng, HsUbiquitin: 5 g, FBXL18: 0.5 g, and Flag-eSCR-myc: 0.8 g. In order to ensure a consistent start time for parallel reactions, the components were added in the following order during the activity analysis test: HsUbcH5C, HsUbiquitin, SCF$^{FBXL18}$ complex (including the two components FBXL18 and Flag-eSCR-myc, where an addition order of the components was not strictly restricted), HsE1, and 20×reaction buffer (formula: 1 M Tris (pH 7.4), 200 mM MgCl$_2$, 100 mM ATP, and 40 mM DTT).

The in vitro ubiquitination assay sample was conducted at 28° C. for 2 h; after the reaction was completed, 6×SDS sample loading buffer was added to terminate the reaction; and an active reaction sample was subjected to SDS-PAGE and WB analysis, then incubated with an anti-Ubiquitin antibody and an anti-mouse-HRP antibody successively, and subjected to development.

Figure 8A:
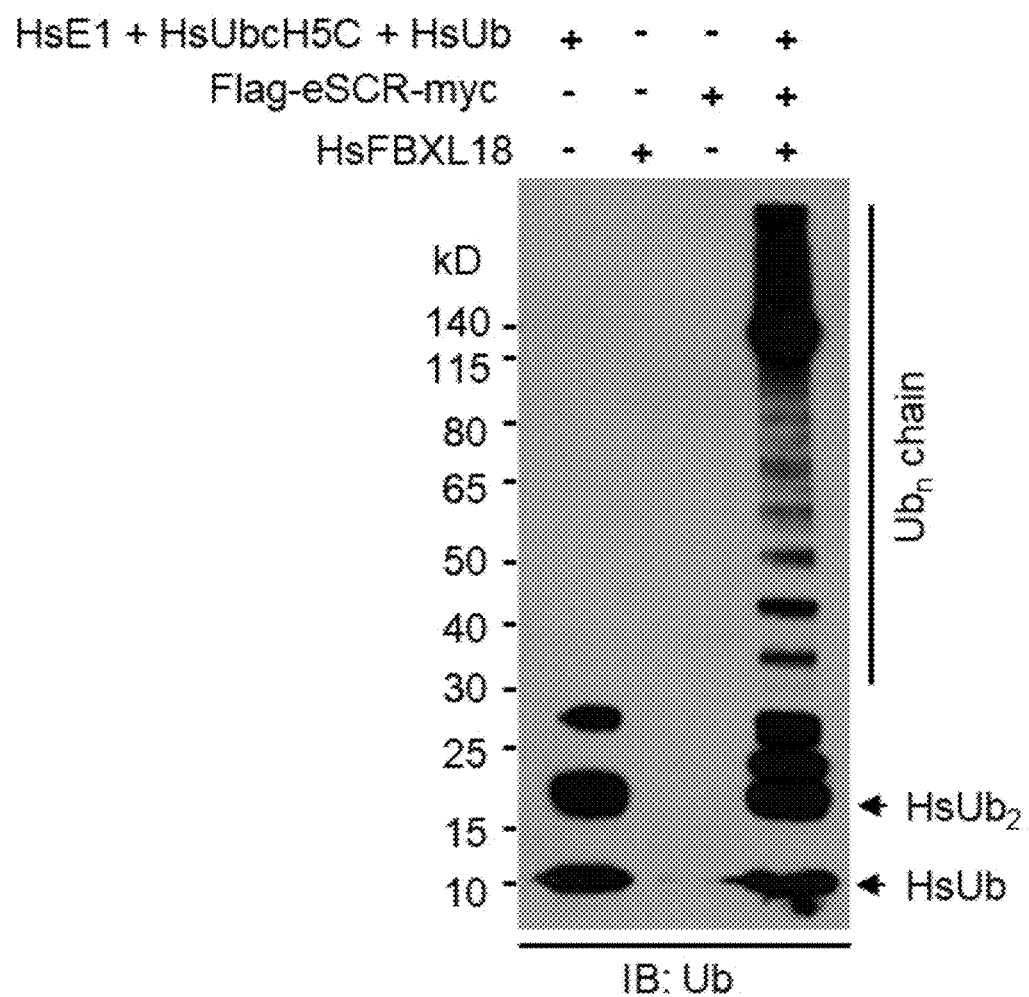
FIGS. 8A-B show the preparation of an active eSCF E3 ligase with the fusion protein Flag-eSCR-myc and an F-box protein derived from other species through reconstitution, where

The experimental results showed that, in the presence of HsE1, HsUbiquitin, and HsUbcH5C, the eSC$^{FFBXL18}$ E3 ligase could be effectively prepared with the fusion protein Flag-eSCR-myc and the protein FBXL18 through active reconstitution to form a polyubiquitin chain (In FIG. 8A).

Example 4 Preparation of a Human-Derived eSCF$^{CDC4}$ E3 Ligase with a Fusion Protein Flag-eSCR-Myc Through In Vitro Reconstitution 4.1 Preparation of an eSCF$^{CDC4}$ E3 Ligase with the Fusion Protein Flag-eSCR-Myc and a Human-Derived F-Box Protein Through In Vitro Reconstitution A system for preparing the human-derived SCF$^{CDC4}$ E3 ligase with the fusion protein Flag-eSCR-myc through in vitro reconstitution was obtained by adding MgCl$_2$, DTT, ATP, HsE1, HsCDC34 (Abnova, catalog No.: H00000997-P01), HsUbiquitin, HsCDC4 (Abnova, catalog No.: H00055294-P01), and the Flag-eSCR-myc in Example 1 to 50 mM Tris-HCl buffer (pH 7.4), a reaction system usually had a volume of 30 L, and a content of each component in the reaction system was as follows: MgCl$_2$: 10 mM, DTT: 2 mM, ATP: 5 mM, HsE1: 50 ng, HsCDC34: 200 ng, HsUbiquitin: 5 g, CDC4: 0.5 g, and Flag-eSCR-myc: 0.8 g. In order to ensure a consistent start time for parallel reactions, the components were added in the following order during the activity analysis test: HsCDC34, HsUbiquitin, SCF$^{CDC4}$ complex (including the two components CDC4 and Flag-eSCR-myc, where an addition order of the components was not strictly restricted), HsE1, and 20×reaction buffer (formula: 1 M Tris (pH 7.4), 200 mM MgCl$_2$, 100 mM ATP, and 40 mM DTT).

The in vitro ubiquitination assay sample was conducted at 28° C. for 2 h; after the reaction was completed, 6×SDS sample loading buffer was added to terminate the reaction; and an active reaction sample was subjected to SDS-PAGE and WB analysis, then incubated with an anti-Ubiquitin antibody and an anti-mouse-HRP antibody successively, and subjected to development.

Figure 8B:
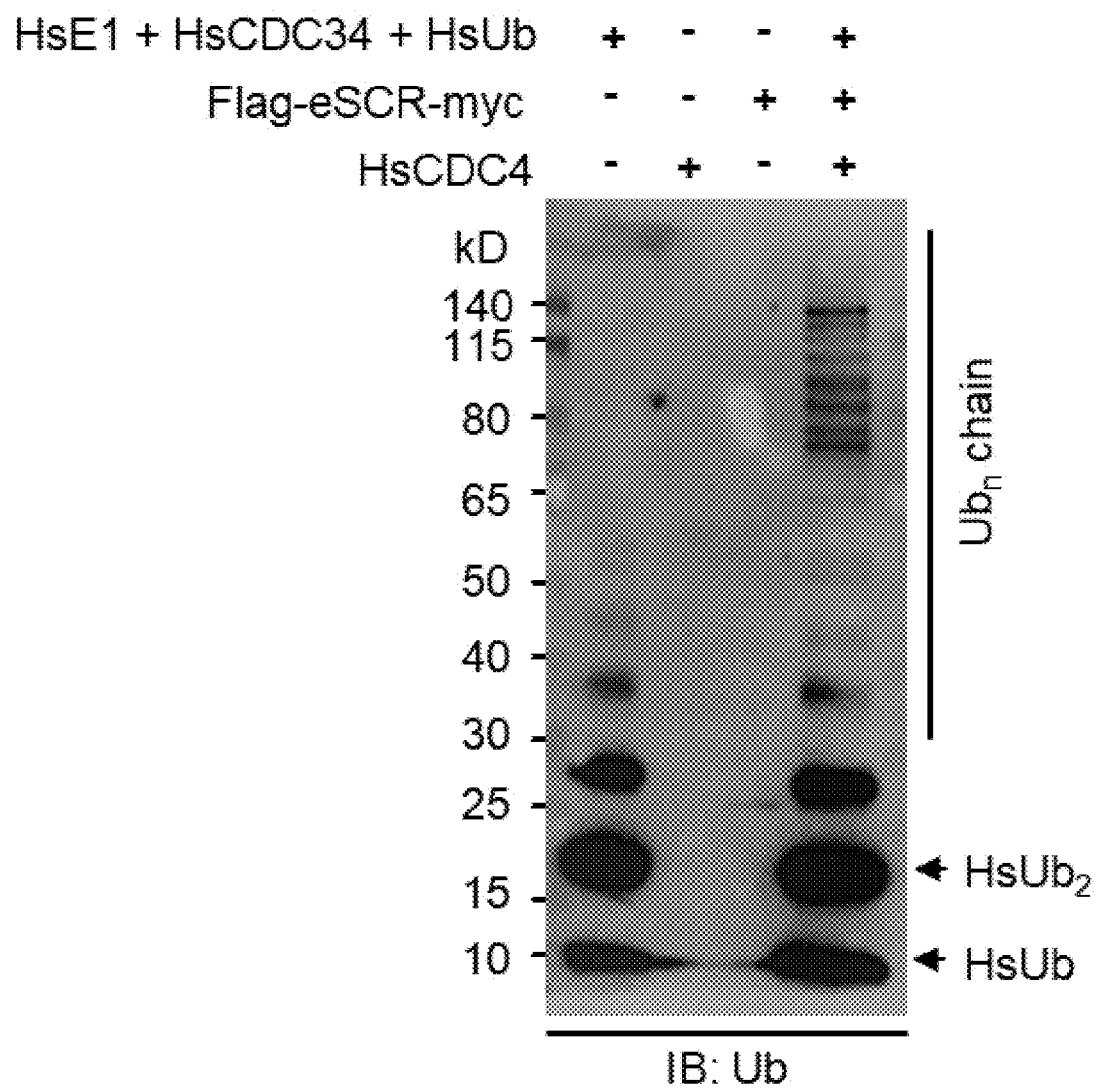

The experimental results showed that, in the presence of HsE1, HsUbiquitin, and HsCDC34, the eSCF$^{CDC4}$ E3 ligase could be effectively prepared with the fusion protein Flag-eSCR-myc and the protein CDC4 through active reconstitution to form a polyubiquitin chain (In FIG. 8B).

4.2 Analysis of Ubiquitination of a Protein Sic1 with an In Vitro Reconstitution System for a Multisubunit eSCF$^{CDC4}$ E3 Ligase The ubiquitination of the protein Sic1 was analyzed with an in vitro reconstitution system for a multisubunit eSCF$^{CDC4}$ E3 ligase, where the in vitro reconstituted ubiquitination assay system was obtained by adding MgCl$_2$, DTT, ATP, His-OsE1, His-OsUBC14, His-OsUbiquitin, D3-Flag, the Flag-eSCR-myc in Example 1, and HsSic1-HA to 50 mM Tris-HCl buffer (pH 7.4), a reaction system usually had a volume of 30 L, and a content of each component in the reaction system was as follows: MgCl$_2$: 10 mM, DTT: 2 mM, ATP: 5 mM, His-OsE1: 50 ng, His-OsUBC14: 200 ng, His-OsUbiquitin: 5 g, D3-Flag: 0.5 g, Flag-eSCR-myc: 0.8 g, and Sic1-HA: 100 ng. In order to ensure a consistent start time for parallel reactions, the components were added in the following order during the activity analysis test: His-OsUBC14, His-OsUbiquitin, Sic1-HA, SCF$^{CDC4}$ complex (including CDC4 and Flag-eSCR-myc, where an addition order of the components was not strictly restricted), His-OsE1, and 20×reaction buffer (formula: 1 M Tris (pH 7.4), 200 mM MgCl$_2$, 100 mM ATP, and 40 mM DTT).

The in vitro ubiquitination assay sample was conducted at 28° C. for 2 h; after the reaction was completed, 6×SDS sample loading buffer was added to terminate the reaction; and an active reaction sample was subjected to SDS-PAGE and WB analysis, then incubated with an anti-HA antibody and an anti-mouse-HRP antibody successively, and subjected to development.

Figure 9:
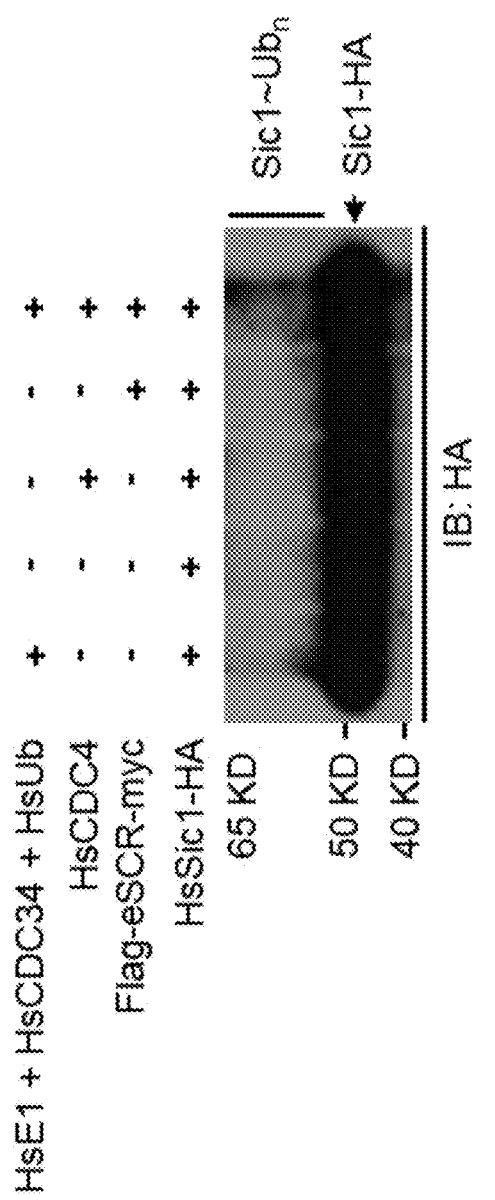
FIG. 9 shows the experimental results of ubiquitination of the substrate protein Sic1-HA by the $eSCF^{CDC4}$ E3 ligase obtained through in vitro reconstitution using a fusion protein Flag-eSCR-myc and a protein CDC4, where the experimental results show that the $eSCF^{CDC4}$ E3 ligase can catalyze the ubiquitination of the substrate protein Sic1-HA.

The experimental results showed that the eSCF$^{CDC4}$ E3 ligase obtained through reconstitution with the fusion protein Flag-eSCR-myc could ubiquitinate the protein Sic1 (FIG. 9). The above results showed that the eSCF$^{CDC4}$ E3 ligase obtained through reconstitution with the fusion protein Flag-eSCR-myc not only had the biological activity of the E3 ligase, but also could effectively catalyze the ubiquitination of the substrate protein Sic1.

The HsSic1-HA was prepared through the following steps:

i1) With the synthesized HsSic1 gene as a template, PHHsSic1F and PHHsSic1HAR primers (Table 2) were used to clone the gene fragment HsSic1-HA with the tag encoding the HA fusion protein to a pFast Bac Dual vector according to the step c1) to obtain a plasmid pFastBac Dual-pPH:HsSic1-HA, where endonucleases SpeI and XbaI were used to construct the plasmid; and a gene encoding the protein HsSic1 had an accession number of AAH01670 (update date: 2013.1) (www.ncbi.nlm.nih.gov/genbank).

i2) The protein HsSic1-HA was expressed with an insect baculovirus expression system according to steps c2) to c4) and purified according to steps c5) to c9), where anti-HA agarose (Sigma, catalog No.: A2095) was used for the purification of the protein HsSic1-HA and 500 ng/mL 1×HA peptide (Sigma, catalog No.: 12149) was used for the elution of the protein HsSic1-HA; and finally, the purified protein HsSic1-HA was dispensed and stored at −80° C. for later use.

The above examples show that the establishment of an in vitro reconstituted ubiquitination assay system for a multisubunit SCF E3 ligase using the fusion protein Flag-eSCR-myc simplifies the composition of the active system, enables the cross-species compatibility, makes the system have promising application prospects, and is of important biological significance for studying the molecular mechanism between a multisubunit SCF E3 ligase and a substrate protein thereof in eukaryotes.

The disclosure has been described in detail above. Without departing from the purpose and scope of the disclosure and without unnecessary experimental conditions, the disclosure can be implemented by those skilled in the art in a wide range under equivalent parameters, concentrations, and conditions. Although specific examples of the disclosure have been given, it should be understood that the disclosure can be further modified. In summary, according to the principle of the disclosure, the disclosure is intended to encompass any change to, use of, or modification to the disclosure, including changes made using conventional techniques known in the art, which have departed from the scope disclosed in the disclosure. Application of some basic features can be done in accordance with the scope of the following appended claims.

Sequence Listing Information:
  DTD Version: V1_3
  File Name: GWP20221202172_seqlist.xml
  Software Name: WIPO Sequence
  Software Version: 2.2.0
  Production Date: 2023 Apr. 23
General Information:
  Current application/Applicant file reference: GWP20221202172
  Earliest priority application/IP Office: CN
  Earliest priority application/Application number: 202210696862.7
  Earliest priority application/Filing date: 2022-06-20
  Applicant name: Institute of Genetics and Developmental Biology, CAS
  Applicant name/Language: en
  Invention title: METHOD FOR PREPARING MULTISUBUNIT SCF E3 LIGASE WITH FUSION PROTEIN THROUGH IN VITRO RECONSTITUTION, AND USE OF MULTISUBUNIT SCF E3 LIGASE (en)
  Sequence Total Quantity: 45
Sequences:
  Sequence Number (ID): 1
  Length: 3219
  Molecule Type: DNA
  Features Location/Qualifiers:
    source, 1..3219
      mol_type, other DNA
      note, eSCR fusion gene
      organism, synthetic construct
  Residues:

```
atggactaca aagacgatga cgacaagatg gggccgagg cggagacgaa ggcgatgatc    60
accctccgca gctgcgaggg ccaggtgttc gaggtcgcgg aggccgtggc catggagtcc   120
cagaccatcc gccacatgat cgaggacaag tgcgccgaca ccggcatccc gctccccaac   180
gtctccgcca agatcctctc caaggtaatc gagtactgca gcaagcacgt cgaggcgcgc   240
ggcggggcgg ccgccgccgc cgacggcgac gcccccgccc ccgccgccgt ggaggccaac   300
aaggccgtcg aggacagagct caagacgttc gacgccgagt tcgtcaaggt cgaccagtcc   360
accctcttcg atctcatcct ggctgcaaac tacctcaaca tcaagggact gctggatctg   420
acctgccaga ccgtggctga catgatcaag gggaagacac cagaggagat ccgcaagacc   480
ttcaacatca agaatgactt caccccgag gaagaagagg aggtgaggag ggagaaccag   540
tgggccttcg aaggaggatc aggaatggcg acccacgagc ggaagacgat cgatctggag   600
caggggtggg agttcatgca gaagggcatc accaagctga agaacatcct cgaggggaag   660
cccgaacccc agttcagctc cgaggactac atgatgctct acacgacgat ttacaacatg   720
tgcacgcaga agccgccgca cgactactcg cagcagctct acgaagaagta ccgcgagtcc   780 ttcgaggagt acatcacgtc catggtctta ccttcattaa gagagaaaca tgatgagttt   840
```

-continued

```
atgctgagag agctagtaaa acggtggtca aaccataaag tgatggttcg gtggctatca    900
cgcttcttcc attatcttga tcggtacttt atttcaagga ggtccctacc acaactaagt    960
gaagttgggc ttagctgttt ccgggatctg gtatatcaag agatcaaagg aaaagtaaaa   1020
agtgcggtga tatccttgat agatcaagaa cgtgagggtg aacaaattga tagggccctg   1080
ttaaagaatg ttctggatat atttgttgag attggcttga ctagcatgga ctactacgaa   1140
aatgattttg aagatttctt gctcaaagat actgcagact attactctat aaaagcccag   1200
acctggattc ttgaggactc ttgtccagat tacatgttaa aggcagagga gtgtctgaaa   1260
agggagaaag agcgagttgc tcattatttg cactccagta gtgaacagaa gttgttggag   1320
aaagtgcaac atgagttgct aactcaatac gcaagtcagc tcctggagaa ggagcattct   1380
ggatgccatg cattgcttcg tgatgacaag gttgatgatc tctctagaat gtacaggctc   1440
ttttccagaa taactcgtgg tttagaacct gtttctcaaa tatttaagca gcatgttact   1500
aatgagggca ctgccttagt gaagcaagcc gaagatgctg ctagtaataa gaagccagag   1560
aagaaggaga tagttggttt acaggaacag gttttttgtcc ggaaaatcat tgagcttcat   1620
gacaagtatg tagcttatgt tacggattgt tttcaggggc acactctctt ccataaggca   1680
cttaaggagg cttttgaagt tttttgcaac aaaggtgttt ctggcagttc aagtgctgaa   1740
ttactagcta ccttctgtga caatatctta agaaaggcg gtagtgaaaa gcttagtgat   1800
gaagcaattg aagatacct tgagaaggtt gtaaggttac ttgcctacat tagtgacaag   1860
gacttgtttg ctgagttcta tagaaagaag cttgcaagga gattgctttt tgacaagagt   1920
gctaatgatg aacatgagag aagcatcctt accaagctaa agcaacaatg tggagggcag   1980
ttcacttcca aaatggaggg catggttact gatctcactg tggcaagaga tcaccaggct   2040
aaatttgaag agttcataag cacacactca gagttgaatc ctggaatagc cttagctgtt   2100
actgtcctca caacaggatt ttggccaagt tacaaatctt ttgatataaa tctacctgca   2160
gaaatggtga atgtgtaga ggttttcaag gagtttttacc aaacaagaac aaaacacagg   2220
aaacttacct ggatttattc actgggaacc tgtaatatta atgctaaatt tgaggccaaa   2280
actattgagc tcattgttac aacttatcag gctgcattgc tgctgctgtt taatggagtt   2340
gatagactca gctattctga gattgtgaca cagttaaatc tctcagatga tgatgttgtt   2400
cgattgctcc attctctatc ttgtgcaaaa tacaagattc ttagcaaaga accaaataat   2460
agatctattt caccaaatga tgtcttcgag ttcaactcaa agtttactga caagctgcga   2520
agattaaaga tacctcttcc tccagttgat gagaagaaga agtagttga agatgttgat   2580
aaggatcgca gatacgcaat tgatgcatca attgtgcgta ttatgaagag tcgcaaagta   2640
ttgggtcatc agcaacttgt gatggaatgt gtggagcagc ttgacgcat gtttaagcct   2700
gacttcaagg caataaagaa gcgaattgag gatcttatca aagggatta cttggagagg   2760
gataaagaca acccaaatgt gtacagatac ttggctggag gatcaggaat gtcggccatg   2820
gagaccgaca tcaacgcgcc gccgccccc gccccgccc ccgccggcgc cggcgaggga   2880
tcctcctctg ccgccggccc ctcctcccgc aagcccaaca agcgcttcga gatcaagaag   2940
tggaacgccg tcgcgctctg ggcatgggat atcgtcgtcg acaactgcgc catctgccgc   3000
aaccacatca tggatctatg catcgagtgc aggcgaacc aggccagcgc caccagtgag   3060
gagtgcactg tcgcttgggg tgtctgtaat catgcttttc acttccattg catcagcagg   3120
tggctcaaga ctcgccaagt gtgcccgtta gataacagtg aatgggaatt tcagaaatat   3180
gggcacgaac aaaaactcat ctcagaagag gatctgtag                         3219
```

Sequence Number (ID): 2
Length: 1072
Molecule Type: AA
Features Location/Qualifiers:
    source, 1..1072
mol_type, protein
note, eSCR fusion protein
organism, synthetic construct
    Residues:

```
MDYKDDDDKM AAEAETKAMI TLRSCEGQVF EVAEAVAMES QTIRHMIEDK CADTGIPLPN    60

VSAKILSKVI EYCSKHVEAR GGAAAAADGD APAPAAVEAN KAVEDELKTF DAEFVKVDQS   120

TLFDLILAAN YLNIKGLLDL TCQTVADMIK GKTPEEIRKT FNIKNDFTPE EEEEVRRENQ   180

WAFEGGSGMA THERKTIDLE QGWEFMQKGI TKLKNILEGK PEPQFSSEDY MMLYTTIYNM   240

CTQKPPHDYS QQLYEKYRES FEEYITSMVL PSLREKHDEF MLRELVKRWS NHKVMVRWLS   300

RFFHYLDRYF ISRRSLPQLS EVGLSCFRDL VYQEIKGKVK SAVISLIDQE REGEQIDRAL   360

LKNVLDIFVE IGLTSMDYYE NDFEDFLLKD TADYYSIKAQ TWILEDSCPD YMLKAEECLK   420

REKERVAHYL HSSSEQKLLE KVQHELLTQY ASQLLEKEHS GCHALLRDDK VDDLSRMYRL   480

FSRITRGLEP VSQIFKQHVT NEGTALVKQA EDAASNKKPE KKEIVGLQEQ VFVRKIIELH   540

DKYVAYVTDC FQGHTLFHKA LKEAFEVFCN KGVSGSSSAE LLATFCDNIL KKGGSEKLSD   600

EAIEDTLEKV VRLLAYISDK DLFAEFYRKK LARRLLEDKS ANDEHERSIL TKLKQQCGGQ   660

FTSKMEGMVT DLTVARDHQA KFEEFISTHS ELNPGIALAV TVLTTGFWPS YKSFDINLPA   720

EMVKCVEVFK EFYQTRTKHR KLTWIYSLGT CNINAKFEAK TIELIVTTYQ AALLLLFNGV   780

DRLSYSEIVT QLNLSDDDVV RLLHSLSCAK YKILSKEPNN RSISPNDVFE FNSKFTDKLR   840

RLKIPLPPVD EKKKVVEDVD KDRRYAIDAS IVRIMKSRKV LGHQQLVMEC VEQLGRMFKP   900

DFKAIKKRIE DLITRDYLER DKDNPNVYRY LAGGSGMSAM ETDINAPPPP APAPAGAGEG   960

SSSAAGPSSR KPNKRFEIKK WNAVALWAWD IVVDNCAICR NHIMDLCIEC QANQASATSE  1020

ECTVAWGVCN HAFHFHCISR WLKTRQVCPL DNSEWEFQKY GHEQKLISEE DL          1072
```

Sequence Number (ID): 3
Length: 5
Molecule Type: AA
Features Location/Qualifiers:
    source, 1..5
        mol_type, protein
        note, Poly-Arg tag
        organism, synthetic construct
Residues:

```
                RRRRR               5
```

Sequence Number (ID): 4
Length: 6
Molecule Type: AA
Features Location/Qualifiers:
    source, 1..6
        mol_type, protein
        note, Poly-His tag
        organism, synthetic construct
Residues:

```
                HHHHHH              6
```

Sequence Number (ID): 5
Length: 8
Molecule Type: AA
Features Location/Qualifiers:
    source, 1..8
        mol_type, protein
        note, Flag tag
        organism, synthetic construct
Residues:

```
                DYKDDDDK            8
```

Sequence Number (ID): 6
Length: 8
Molecule Type: AA
Features Location/Qualifiers:
    source, 1..8
        mol_type, protein
        note, Strep-tag II
        organism, synthetic construct
Residues:

```
                WSHPQFEK            8
```

Sequence Number (ID): 7
Length: 10
Molecule Type: AA

Features Location/Qualifiers:
　source, 1..10
　　mol_type, protein
　　note, c-myc tag
　　organism, synthetic construct
Residues:

EQKLISEEDL　　　　10

Sequence Number (ID): 8
Length: 54
Molecule Type: DNA
Features Location/Qualifiers:
　source, 1..54
　　mol_type, other DNA
　　note, Primer PHSCRFLAGF
　　organism, synthetic construct
Residues:

tttgaattca tggactacaa agacgatgac　　54
　gacaagatgg cggccgaggc ggag

Sequence Number (ID): 9
Length: 60
Molecule Type: DNA
Features Location/Qualifiers:
　source, 1..60
　　mol_type, other DNA
　　note, Primer PHSCRFLAGR
　　organism, synthetic construct
Residues:

tttactagtc tacagatcct cttctgagat gagttttgt　　60
tcgtgcccat atttctgaaa

Sequence Number (ID): 10
Length: 46
Molecule Type: DNA
Features Location/Qualifiers:
　source, 1..46
　　mol_type, other DNA
　　note, Primer CUL1K688AF
　　organism, synthetic construct
Residues:

gcatcaattg tgcgtattat ggcgagtcgc　　46
　aaagtattgg gtcatc

Sequence Number (ID): 11
Length: 46
Molecule Type: DNA
Features Location/Qualifiers:
　source, 1..46
　　mol_type, other DNA
　　note, Primer CUL1K688AR
　　organism, synthetic construct
Residues:

gatgacccaa tactttgcga ctcgccataa　　46
　tacgcacaat tgatgc

Sequence Number (ID): 12
Length: 17
Molecule Type: DNA
Features Location/Qualifiers:
　source, 1..17
　　mol_type, other DNA
　　note, Primer M13F
　　organism, synthetic construct
Residues:

gttttcccag tcacgac　　17

Sequence Number (ID): 13
Length: 17
Molecule Type: DNA
Features Location/Qualifiers:
　source, 1..17
　　mol_type, other DNA
　　note, Primer M13R
　　organism, synthetic construct
Residues:

caggaaacag ctatgac　　17

Sequence Number (ID): 14
Length: 53
Molecule Type: DNA
Features Location/Qualifiers:
　source, 1..53
　　mol_type, other DNA
　　note, Primer GWOSUBF
　　organism, synthetic construct
Residues:

ggggacaagt ttgtacaaaa aagcaggctt tatgcagatc　　53
tttgtgaaga cat

Sequence Number (ID): 15
Length: 52
Molecule Type: DNA
Features Location/Qualifiers:
　source, 1..52
　　mol_type, other DNA
　　note, Primer GWOSUBR
　　organism, synthetic construct
Residues:

ggggaccact tgtacaaga aagctgggtt ttagccacca　　52
cggaggcgga gg

Sequence Number (ID): 16
Length: 58
Molecule Type: DNA
Features Location/Qualifiers:
　source, 1..58
　　mol_type, other DNA
　　note, Primer GWOSUBC14F
　　organism, synthetic construct Residues:

ggggacaagt tgtacaaaa aagcaggctt tatggcgtca agaggatac agaaggag 58

Sequence Number (ID): 17
Length: 55
Molecule Type: DNA
Features Location/Qualifiers:
    source, 1..55
        mol_type, other DNA
        note, Primer GWOSUBC14R
        organism, synthetic construct
Residues:

ggggaccact ttgtacaaga aagctgggtt ctacatggcg tacctctgag tccag 55

Sequence Number (ID): 18
Length: 56
Molecule Type: DNA
Features Location/Qualifiers:
    source, 1..56
        mol_type, other DNA
        note, Primer GWOSUBC18F
        organism, synthetic construct
Residues:

ggggacaagt tgtacaaaa aagcaggctt tatggcaagc aaaaggattc agaagg 56

Sequence Number (ID): 19
Length: 55
Molecule Type: DNA
Features Location/Qualifiers:
    source, 1..55
        mol_type, other DNA
        note, Primer GWOSUBC18R
        organism, synthetic construct
Residues:

ggggaccact ttgtacaaga aagctgggtt ctaacccatt gcgtatttct gggtc 55

Sequence Number (ID): 20
Length: 56
Molecule Type: DNA
Features Location/Qualifiers:
    source, 1..56
        mol_type, other DNA
        note, Primer GWOSE1F
        organism, synthetic construct
Residues:

ggggacaagt tgtacaaaa aagcaggctt tatgcttccg acgaagagag cgaacg 56

Sequence Number (ID): 21
Length: 55
Molecule Type: DNA
Features Location/Qualifiers:
    source, 1..55
        mol_type, other DNA
        note, Primer GWOSE1R
        organism, synthetic construct
Residues:

ggggaccact ttgtacaaga aagctgggtt ctaccggaag taaatggaga tgaga 55

Sequence Number (ID): 22
Length: 55
Molecule Type: DNA
Features Location/Qualifiers:
    source, 1..55
        mol_type, other DNA
        note, Primer GWD14F
        organism, synthetic construct
Residues:

ggggacaagt tgtacaaaa aagcaggctt tatgctgcga tcgacgcatc cgccg    55

Sequence Number (ID): 23
Length: 54
Molecule Type: DNA
Features Location/Qualifiers:
    source, 1..54
        mol_type, other DNA
        note, Primer GWD14R
        organism, synthetic construct
Residues:

ggggaccact tgtacaaga aagctgggtt ttagtaccgg gcgagagcgc ggcg    54

Sequence Number (ID): 24
Length: 56
Molecule Type: DNA
Features Location/Qualifiers:
    source, 1..56
        mol_type, other DNA
        note, Primer GWD3F
        organism, synthetic construct
Residues:

ggggacaagt tgtacaaaa aagcaggctt tatggcggaa gaggaggagg tggagg    56

Sequence Number (ID): 25
Length: 55
Molecule Type: DNA
Features Location/Qualifiers:
    source, 1..55
        mol_type, other DNA
        note, Primer GWD3R
        organism, synthetic construct
Residues:

ggggaccact tgtacaaga aagctgggtt ctaatcatca atttgccggc tgttc    55

Sequence Number (ID): 26
Length: 27
Molecule Type: DNA
Features Location/Qualifiers:
    source, 1..27
        mol_type, other DNA
        note, Primer PHD3FF
        organism, synthetic construct
Residues:

tttggatcca tggcggaaga ggaggag    27

Sequence Number (ID): 27
Length: 55
Molecule Type: DNA
Features Location/Qualifiers:
    source, 1..55
        mol_type, other DNA
        note, Primer PHD3FR
        organism, synthetic construct
Residues:

tttgaattcc tacttgtcgt catcgtcttt gtagtcatca tcaatttgcc ggctg    55

Sequence Number (ID): 28
Length: 28
Molecule Type: DNA
Features Location/Qualifiers:
    source, 1..28
        mol_type, other DNA
        note, Primer PHCUL1FF
        organism, synthetic construct
Residues:

```
    tttgaattca tggcgaccca cgagcgga      28
```

Sequence Number (ID): 29
Length: 55
Molecule Type: DNA
Features Location/Qualifiers:
    source, 1..55
        mol_type, other DNA
        note, Primer PHCUL1FR
        organism, synthetic construct
Residues:

```
tttactagtt cacttgtcgt catcgtcttt gtagtcagcc aagtatctgt acaca   55
```

Sequence Number (ID): 30
Length: 65
Molecule Type: DNA
Features Location/Qualifiers:
    source, 1..65
        mol_type, other DNA
        note, Primer GWSKP1F
        organism, synthetic construct
Residues:

```
ggggacaagt ttgtacaaaa aagcaggctt tatggcggcc gaggcggaga cgaaggcgat   60
gatca                                                              65
```

Sequence Number (ID): 31
Length: 63
Molecule Type: DNA
Features Location/Qualifiers:
    source, 1..63
        mol_type, other DNA
        note, Primer GWSKP1R
        organism, synthetic construct
Residues:

```
ggggaccact ttgtacaaga aagctgggtt tcattcgaag gcccactggt tctccctcct   60
cac                                                                63
```

Sequence Number (ID): 32
Length: 27
Molecule Type: DNA
Features Location/Qualifiers:
    source, 1..27
        mol_type, other DNA
        note, Primer P10SKP1F
        organism, synthetic construct
Residues:

```
    tttgctagca tggcggccga ggcggag      27
```

Sequence Number (ID): 33
Length: 29
Molecule Type: DNA
Features Location/Qualifiers:
    source, 1..29
        mol_type, other DNA
        note, Primer P10SKP1R
        organism, synthetic construct
Residues:

```
    tttggtacct cattcgaagg cccactggt      29
```

Sequence Number (ID): 34
Length: 58
Molecule Type: DNA

Features Location/Qualifiers:
    source, 1..58
        mol_type, other DNA
        note, Primer GWRBX1F
        organism, synthetic construct
Residues:

ggggacaagt tgtacaaaa aagcaggctt tatgtcggcc atggagaccg acatcaac  58

Sequence Number (ID): 35
Length: 55
Molecule Type: DNA
Features Location/Qualifiers:
    source, 1..55
        mol_type, other DNA
        note, Primer GWRBX1R
        organism, synthetic construct
Residues:

ggggaccact tgtacaaga aagctgggtt ctagtgccca tatttctgaa attcc  55

Sequence Number (ID): 36
Length: 29
Molecule Type: DNA
Features Location/Qualifiers:
    source, 1..29
        mol_type, other DNA
        note, Primer P10RBX1F
        organism, synthetic construct
Residues:

tttgctagca tgtcggccat ggagaccga     29

Sequence Number (ID): 37
Length: 30
Molecule Type: DNA
Features Location/Qualifiers:
    source, 1..30
        mol_type, other DNA
        note, Primer P10RBX1R
        organism, synthetic construct
Residues:

tttggtaccc tagtgcccat atttctgaaa    30

Sequence Number (ID): 38
Length: 54
Molecule Type: DNA
Features Location/Qualifiers:
    source, 1..54
        mol_type, other DNA
        note, Primer GWGID2F
        organism, synthetic construct
Residues:

ggggacaagt tgtacaaaa aagcaggctt tatgaagttc cgctctgatt cgtc  54

Sequence Number (ID): 39
Length: 55
Molecule Type: DNA
Features Location/Qualifiers:
    source, 1..55
        mol_type, other DNA
        note, Primer GWGID2R
        organism, synthetic construct Residues:

```
ggggaccact tgtacaaga aagctgggtt ctacccgcat tggcccctc cattc    55
```

Sequence Number (ID): 40
Length: 34
Molecule Type: DNA
Features Location/Qualifiers:
    source, 1..34
        mol_type, other DNA
        note, Primer PHGID2FF
        organism, synthetic construct
Residues:

```
   tttgaattca tgaagttccg ctctgattcg tcag    34
```

Sequence Number (ID): 41
Length: 63
Molecule Type: DNA
Features Location/Qualifiers:
    source, 1..63
        mol_type, other DNA
        note, Primer PHGID2FR
        organism, synthetic construct
Residues:

```
ttttctagat cacttgtcgt catcgtcttt gtagtccccg cattggcccc ctccattctt    60
atc    63
```

Sequence Number (ID): 42
Length: 40
Molecule Type: DNA
Features Location/Qualifiers:
    source, 1..40
        mol_type, other DNA
        note, Primer PHD53INF
        organism, synthetic construct
Residues:

```
catcgggcgc ggatccatgc ccactccggt ggccgccgcg    40
```

Sequence Number (ID): 43
Length: 68
Molecule Type: DNA
Features Location/Qualifiers:
    source, 1..68
        mol_type, other DNA
        note, Primer PHD53INHAR
        organism, synthetic construct
Residues:

```
gtaggcctt gaattctcaa gcgtaatctg gaacatcgta tgggtaacaa tctagaatta    60
ttcttggc    68
```

Sequence Number (ID): 44
Length: 40
Molecule Type: DNA
Features Location/Qualifiers:
    source, 1..40
        mol_type, other DNA
        note, Primer PHHsSic1F
        organism, synthetic construct
Residues:

```
cgacgagctc actagtatgg acgggactat taaggaggct    40
```

Sequence Number (ID): 45
Length: 70
Molecule Type: DNA
Features Location/Qualifiers:
    source, 1..70
        mol_type, other DNA
        note, Primer PHHsSic1HAR
        organism, synthetic construct Residues:

```
gactgcaggc tctagatcaa gcgtaatctg gaacatcgta tgggtagtag tagctgccta  60
agtgtgaagg                                                         70
```

END

END

---

What is claimed is:

1. A method of preparing a multisubunit SKP1-Cullin1-RBX1-F-box protein (SCF) E3 ligase, comprising the step of combining an engineered SKP1-Cullin1-RBX1 (eSCR) fusion protein with an F-box protein in a reaction system to obtain the E3 ligase,
   wherein the eSCR fusion protein is a fusion protein with the amino acid sequence from position 10 to position 1062 of SEQ ID NO. 2.

2. The method according to claim 1, wherein the reaction system further comprises at least one of 50 mM Tris-HCl buffer with a pH of 7.4, $MgCl_2$, DTT, ATP, or combinations thereof.

3. The method according to claim 1, wherein the combining is conducted at 22° C. to 37° C.

4. The method according to claim 1, wherein the combining is conducted for 1 h to 2 h.

5. A multisubunit SCF E3 ligase, comprising an eSCR fusion protein with the amino acid sequence from position 10 to position 1062 of SEQ ID NO: 2, and an F-box protein.

6. A reagent kit, comprising the multisubunit SCF E3 ligase according to claim 5.

7. The reagent kit according to claim 6, wherein the reagent kit further comprises at least one of 50 mM Tris-HCl buffer with a pH of 7.4, $MgCl_2$, DTT, ATP, ubiquitin-activating enzyme (UAE) E1, ubiquitin-conjugating enzyme (UCE) E2, a ubiquitin monomer, or combinations thereof.

* * * * *

SEQUENCE LISTING

```
Sequence total quantity: 45
SEQ ID NO: 1            moltype = DNA   length = 3219
FEATURE                 Location/Qualifiers
source                  1..3219
                        mol_type = other DNA
                        note = eSCR fusion gene
                        organism = synthetic construct
SEQUENCE: 1
atggactaca aagacgatga cgacaagatg gcggccgagg cggagacgaa ggcgatgatc   60
accctccgca gctgcgaggg ccaggtgttc gaggtcgcgg aggccgtggc catggagtcc  120
cagaccatcc gccacatgat cgaggacaag tgcgccgaca ccggcatccc gctccccaac  180
gtctccgcca agatcctctc caaggtaatc gagtactgca gcaagcacgt cgaggcgcgc  240
ggcggggcgg ccgccgccgc cgacggcgac gcccccgccc ccgccgccgt ggaggccaac  300
aaggccgtcg aggacgagct caagacgttc gacgccgagt cgtcaaggt cgaccagtcc   360
accctcttcg atctcatcct ggctgcaaac tacctcaaca tcaagggact gctggatctg  420
acctgccaga ccgtggctga catgatcaag gggaagacac caggagat ccgcaagacc   480
ttcaacatca agaatgactt cacccccgag gaagaagagg aggtgaggag ggagaaccag  540
tgggccttcg aaggaggatc aggaatggcg acccacgagc ggaagacgat cgatctggag  600
caggggtggg agttcatgca gaagggcatc accaagctga agaacatcct cgaggggaag  660
cccgaacccc agttcagctc cgaggactac atgatgctct acacgacgat ttacaacatg  720
tgcacgcaga agccgccgca cgactactcg cagcagctct acgagaagta ccgcgagtcc  780
ttcgaggagt acatcacgtc catggtctta ccttcattaa gagagaaaca tgatgagttt  840
atgctgagag agctagtaaa acggtggtca aaccataaag tgatggttcg gtggctatca  900
cgcttcttcc attatcttga tcggtacttt atttcaagga ggtccctacc acaactaagt  960
gaagttgggc ttagctgttt ccgggatctg gtatatcaag agatcaaagg aaaagtaaaa 1020
agtgcggtga tatccttgat agatcaagaa cgtgagggtg aacaaattga tagggccctg 1080
ttaaagaatg ttctggatat atttgttgag attggcttga ctagcatgga ctactacgaa 1140
aatgattttg aagatttctt gctcaaagat actgcagact attactctat aaaagcccag 1200
acctggattc ttgaggactc ttgtccagat tacatgttaa aggcagagga gtgtctgaaa 1260
agggagaaag agcgagttgc tcattatttg cactccagta gtgaacagaa gttgttggag 1320
aaagtgcaac atgagttgct aactcaatac gcaagtcagc tcctgagaa ggagcattct  1380
ggatgccatg cattgcttcg tgatgacaag gttgatgatc tctctagaat gtacaggctc 1440
ttttccagaa taactcgtgg tttagaacct gtttctcaaa tatttaagca gcatgttact 1500
aatgagggca ctgccttagt gaagcaagcc gaagatgctg ctagtaataa gaagccagag 1560
aagaaggaga tagttggttt acaggaacag gttttgtcc ggaaaatcat tgagcttcat  1620
gacaagtatg tagcttatgt tacgattgt tttcagggc acactctctt ccataaggca  1680
cttaaggagg ctttttgaagt tttttgcaac aaaggtgttt ctggcagttc aagtgctgaa 1740
ttactagcta ccttctgtga caatatctta aagaaggcg gtagtgaaaa gcttagtgat 1800
gaagcaattg aagatacct tgagaaggtt gtaaggttac ttgcctacat tagtgacaag 1860
gacttgtttg ctgagttcta tagaaagaag cttgcaagga gattgcttt tgacaagagt 1920
gctaatgatg aacatgagag aagcatcctt accaagctaa agcaacaatg tggagggcag 1980
ttcacttcca aaatggaggg catggttact gatctcactg tggcaagaga tcaccaggct 2040
aaatttgaag agttcataag cacacactca gagttgaatc ctggaatagc cttagctgtt 2100
actgtcctca caacaggatt ttggccaagt tacaaatctt ttgatataaa tctacctgca 2160
gaaatggtga aatgtgtaga ggttttcaag gagttttacc aaacaagaac aaacacagg  2220
aaacttacct ggatttattc actgggaacc tgtaatatta atgctaaatt tgaggccaaa 2280
actattgagc tcattgttac aacttatcag gctgcattgc tgctgctgtt taatggagtt 2340
gatagactca gctattctga gattgtgaca cagttaaatc tctcagatga tgatgttgtt 2400
cgattgctcc attctctatc ttgtgcaaaa tacaagattc ttagcaaaga accaaataat 2460
agatctattt caccaaatga tgtcttcgag ttcaactcaa agttactga caagctgcga 2520
agattaaaga taccctcttcc tccagttgat gagaagaaga agtagtga agatgttgat 2580
aaggatcgca gatacgcaat tgatgcatca attgtgcgta ttatgaagag tcgcaaagta 2640
ttgggtcatc agcaacttgt gatgaatgt gtggagcagc ttggacgcat gtttaagcct 2700
gacttcaagg caataaagaa gcgaattgag gatcttatca caagggatta cttggagagg 2760
gataaagaca acccaaatgt gtacagatac ttggctggag gatcaggaat gtcggccatg 2820
gagaccgaca tcaacgcgcc gccgccccc gccccgccc ccgccggcgc cggcgaggga  2880
tcctcctctg ccgccggccc ctcctcccgc aagcccaaca agcgcttcga gatcaagaag 2940
tggaacgccg tcgcgctctg ggcatgggat atcgtcgtcg acaactgcgc catctgccgc 3000
aaccacatca tggatctatg catcgagtgc caggcgaacc aggccagcgc caccagtgag 3060
gagtgcactg tcgcttgggg gtgtctgtaat catgctttc acttccattg catcagcagg 3120
tggctcaaga ctcgccaagt gtgccgtta gataacagta aatgggaatt tcagaaatat 3180
gggcacgaac aaaactcat ctcagaagag gatctgtag                          3219

SEQ ID NO: 2            moltype = AA    length = 1072
FEATURE                 Location/Qualifiers
source                  1..1072
```

```
                            mol_type = protein
                            note = eSCR fusion protein
                            organism = synthetic construct
SEQUENCE: 2
MDYKDDDDKM AAEAETKAMI TLRSCEGQVF EVAEAVAMES QTIRHMIEDK CADTGIPLPN    60
VSAKILSKVI EYCSKHVEAR GGAAAAADGD APAPAAVEAN KAVEDELKTF DAEFVKVDQS   120
TLFDLILAAN YLNIKGLLDL TCQTVADMIK GKTPEEIRKT FNIKNDFTPE EEEEVRRENQ   180
WAFEGGSGMA THERKTIDLE QGWEFMQKGI TKLKNILEGK PEPQFSSEDY MMLYTTIYNM   240
CTQKPPHDYS QQLYEKYRES FEEYITSMVL PSLREKHDEF MLRELVKRWS NHKVMVRWLS   300
RFFHYLDRYF ISRRSLPQLS EVGLSCFRDL VYQEIKGKVK SAVISLIDQE REGEQIDRAL   360
LKNVLDIFVE IGLTSMDYYE NDFEDFLLKD TADYYSIKAQ TWILEDSCPD YMLKAEEECLK  420
REKERVAHYL HSSSEQKLLE KVQHELLTQY ASQLLEKEHS GCHALLRDDK VDDLSRMYRL   480
FSRITRGLEP VSQIFKQHVT NEGTALVKQA EDAASNKKPE KKEIVGLQEQ VFVRKIIELH   540
DKYVAYVTDC FQGHTLFHKA LKEAFEVFCN KGVSGSSSAE LLATFCDNIL KKGGSEKLSD   600
EAIEDTLEKV VRLLAYISDK DLFAEFYRKK LARRLLFDKS ANDEHERSIL TKLKQQCGGQ   660
FTSKMEGMVT DLTVARDHQA KFEEFISTHS ELNPGIALAV TVLTTGFWPS YKSFDINLPA   720
EMVKCVEVFK EFYQTRTKHR KLTWIYSLGT CNINAKFEAK TIELIVTTYQ AALLLLFNGV   780
DRLSYSEIVT QLNLSDDDVV RLLHSLSCAK YKILSKEPNN RSISPNDVFE FNSKFTDKLR   840
RLKIPLPPVD EKKKVVEDVD KDRRYAIDAS IVRIMKSRKV LGHQQLVMEC VEQLGRMFKP   900
DFKAIKKRIE DLITRDYLER DKDNPNVYRY LAGGSGMSAM ETDINAPPPP APAPAGAGEG   960
SSSSAAGPSSR KPNKRFEIKK WNAVALWAWD IVVDNCAICR NHIMDLCIEC QANQASATSE  1020
ECTVAWGVCN HAFHFHCISR WLKTRQVCPL DNSEWEFQKY GHEQKLISEE DL          1072

SEQ ID NO: 3               moltype = AA   length = 5
FEATURE                    Location/Qualifiers
source                     1..5
                           mol_type = protein
                           note = Poly-Arg tag
                           organism = synthetic construct
SEQUENCE: 3
RRRRR                                                                  5

SEQ ID NO: 4               moltype = AA   length = 6
FEATURE                    Location/Qualifiers
source                     1..6
                           mol_type = protein
                           note = Poly-His tag
                           organism = synthetic construct
SEQUENCE: 4
HHHHHH                                                                 6

SEQ ID NO: 5               moltype = AA   length = 8
FEATURE                    Location/Qualifiers
source                     1..8
                           mol_type = protein
                           note = Flag tag
                           organism = synthetic construct
SEQUENCE: 5
DYKDDDDK                                                               8

SEQ ID NO: 6               moltype = AA   length = 8
FEATURE                    Location/Qualifiers
source                     1..8
                           mol_type = protein
                           note = Strep-tag II
                           organism = synthetic construct
SEQUENCE: 6
WSHPQFEK                                                               8

SEQ ID NO: 7               moltype = AA   length = 10
FEATURE                    Location/Qualifiers
source                     1..10
                           mol_type = protein
                           note = c-myc tag
                           organism = synthetic construct
SEQUENCE: 7
EQKLISEEDL                                                            10

SEQ ID NO: 8               moltype = DNA   length = 54
FEATURE                    Location/Qualifiers
source                     1..54
                           mol_type = other DNA
                           note = Primer PHSCRFLAGF
                           organism = synthetic construct
SEQUENCE: 8
tttgaattca tggactacaa agacgatgac gacaagatgg cggccgaggc ggag           54

SEQ ID NO: 9               moltype = DNA   length = 60
FEATURE                    Location/Qualifiers
```

```
source                  1..60
                        mol_type = other DNA
                        note = Primer PHSCRFLAGR
                        organism = synthetic construct
SEQUENCE: 9
tttactagtc tacagatcct cttctgagat gagtttttgt tcgtgcccat atttctgaaa        60

SEQ ID NO: 10           moltype = DNA  length = 46
FEATURE                 Location/Qualifiers
source                  1..46
                        mol_type = other DNA
                        note = Primer CUL1K688AF
                        organism = synthetic construct
SEQUENCE: 10
gcatcaattg tgcgtattat ggcgagtcgc aaagtattgg gtcatc                       46

SEQ ID NO: 11           moltype = DNA  length = 46
FEATURE                 Location/Qualifiers
source                  1..46
                        mol_type = other DNA
                        note = Primer CUL1K688AR
                        organism = synthetic construct
SEQUENCE: 11
gatgacccaa tactttgcga ctcgccataa tacgcacaat tgatgc                       46

SEQ ID NO: 12           moltype = DNA  length = 17
FEATURE                 Location/Qualifiers
source                  1..17
                        mol_type = other DNA
                        note = Primer M13F
                        organism = synthetic construct
SEQUENCE: 12
gttttcccag tcacgac                                                       17

SEQ ID NO: 13           moltype = DNA  length = 17
FEATURE                 Location/Qualifiers
source                  1..17
                        mol_type = other DNA
                        note = Primer M13R
                        organism = synthetic construct
SEQUENCE: 13
caggaaacag ctatgac                                                       17

SEQ ID NO: 14           moltype = DNA  length = 53
FEATURE                 Location/Qualifiers
source                  1..53
                        mol_type = other DNA
                        note = Primer GWOSUBF
                        organism = synthetic construct
SEQUENCE: 14
ggggacaagt ttgtacaaaa aagcaggctt tatgcagatc tttgtgaaga cat               53

SEQ ID NO: 15           moltype = DNA  length = 52
FEATURE                 Location/Qualifiers
source                  1..52
                        mol_type = other DNA
                        note = Primer GWOSUBR
                        organism = synthetic construct
SEQUENCE: 15
ggggaccact ttgtacaaga aagctgggtt ttagccacca cggaggcgga gg                52

SEQ ID NO: 16           moltype = DNA  length = 58
FEATURE                 Location/Qualifiers
source                  1..58
                        mol_type = other DNA
                        note = Primer GWOSUBC14F
                        organism = synthetic construct
SEQUENCE: 16
ggggacaagt ttgtacaaaa aagcaggctt tatggcgtca agaggatac agaaggag           58

SEQ ID NO: 17           moltype = DNA  length = 55
FEATURE                 Location/Qualifiers
source                  1..55
                        mol_type = other DNA
                        note = Primer GWOSUBC14R
                        organism = synthetic construct
SEQUENCE: 17
ggggaccact ttgtacaaga aagctgggtt ctacatggcg tacctctgag tccag             55
```

| | | |
|---|---|---|
| SEQ ID NO: 18 | moltype = DNA   length = 56 | |
| FEATURE | Location/Qualifiers | |
| source | 1..56<br>mol_type = other DNA<br>note = Primer GWOSUBC18F<br>organism = synthetic construct | |
| SEQUENCE: 18 | | |
| ggggacaagt tgtacaaaaa aagcaggctt tatggcaagc aaaaggattc agaagg | | 56 |
| | | |
| SEQ ID NO: 19 | moltype = DNA   length = 55 | |
| FEATURE | Location/Qualifiers | |
| source | 1..55<br>mol_type = other DNA<br>note = Primer GWOSUBC18R<br>organism = synthetic construct | |
| SEQUENCE: 19 | | |
| ggggaccact ttgtacaaga aagctgggtt ctaacccatt gcgtatttct gggtc | | 55 |
| | | |
| SEQ ID NO: 20 | moltype = DNA   length = 56 | |
| FEATURE | Location/Qualifiers | |
| source | 1..56<br>mol_type = other DNA<br>note = Primer GWOSE1F<br>organism = synthetic construct | |
| SEQUENCE: 20 | | |
| ggggacaagt tgtacaaaaa aagcaggctt tatgcttccg acgaagagag cgaacg | | 56 |
| | | |
| SEQ ID NO: 21 | moltype = DNA   length = 55 | |
| FEATURE | Location/Qualifiers | |
| source | 1..55<br>mol_type = other DNA<br>note = Primer GWOSE1R<br>organism = synthetic construct | |
| SEQUENCE: 21 | | |
| ggggaccact ttgtacaaga aagctgggtt ctaccggaag taaatggaga tgaga | | 55 |
| | | |
| SEQ ID NO: 22 | moltype = DNA   length = 55 | |
| FEATURE | Location/Qualifiers | |
| source | 1..55<br>mol_type = other DNA<br>note = Primer GWD14F<br>organism = synthetic construct | |
| SEQUENCE: 22 | | |
| ggggacaagt tgtacaaaaa aagcaggctt tatgctgcga tcgacgcatc cgccg | | 55 |
| | | |
| SEQ ID NO: 23 | moltype = DNA   length = 54 | |
| FEATURE | Location/Qualifiers | |
| source | 1..54<br>mol_type = other DNA<br>note = Primer GWD14R<br>organism = synthetic construct | |
| SEQUENCE: 23 | | |
| ggggaccact ttgtacaaga aagctgggtt ttagtaccgg gcgagagcgc ggcg | | 54 |
| | | |
| SEQ ID NO: 24 | moltype = DNA   length = 56 | |
| FEATURE | Location/Qualifiers | |
| source | 1..56<br>mol_type = other DNA<br>note = Primer GWD3F<br>organism = synthetic construct | |
| SEQUENCE: 24 | | |
| ggggacaagt tgtacaaaaa aagcaggctt tatggcggaa gaggaggagg tggagg | | 56 |
| | | |
| SEQ ID NO: 25 | moltype = DNA   length = 55 | |
| FEATURE | Location/Qualifiers | |
| source | 1..55<br>mol_type = other DNA<br>note = Primer GWD3R<br>organism = synthetic construct | |
| SEQUENCE: 25 | | |
| ggggaccact ttgtacaaga aagctgggtt ctaatcatca atttgccggc tgttc | | 55 |
| | | |
| SEQ ID NO: 26 | moltype = DNA   length = 27 | |
| FEATURE | Location/Qualifiers | |
| source | 1..27<br>mol_type = other DNA<br>note = Primer PHD3FF<br>organism = synthetic construct | |
| SEQUENCE: 26 | | |

```
tttggatcca tggcggaaga ggaggag                                       27

SEQ ID NO: 27           moltype = DNA   length = 55
FEATURE                 Location/Qualifiers
source                  1..55
                        mol_type = other DNA
                        note = Primer PHD3FR
                        organism = synthetic construct
SEQUENCE: 27
tttgaattcc tacttgtcgt catcgtctttt gtagtcatca tcaatttgcc ggctg        55

SEQ ID NO: 28           moltype = DNA   length = 28
FEATURE                 Location/Qualifiers
source                  1..28
                        mol_type = other DNA
                        note = Primer PHCUL1FF
                        organism = synthetic construct
SEQUENCE: 28
tttgaattca tggcgaccca cgagcgga                                      28

SEQ ID NO: 29           moltype = DNA   length = 55
FEATURE                 Location/Qualifiers
source                  1..55
                        mol_type = other DNA
                        note = Primer PHCUL1FR
                        organism = synthetic construct
SEQUENCE: 29
tttactagtt cacttgtcgt catcgtcttt gtagtcagcc aagtatctgt acaca        55

SEQ ID NO: 30           moltype = DNA   length = 65
FEATURE                 Location/Qualifiers
source                  1..65
                        mol_type = other DNA
                        note = Primer GWSKP1F
                        organism = synthetic construct
SEQUENCE: 30
ggggacaagt ttgtacaaaa aagcaggctt tatggcggcc gaggcggaga cgaaggcgat  60
gatca                                                              65

SEQ ID NO: 31           moltype = DNA   length = 63
FEATURE                 Location/Qualifiers
source                  1..63
                        mol_type = other DNA
                        note = Primer GWSKP1R
                        organism = synthetic construct
SEQUENCE: 31
ggggaccact ttgtacaaga aagctgggtt tcattcgaag gcccactggt tctccctcct  60
cac                                                                63

SEQ ID NO: 32           moltype = DNA   length = 27
FEATURE                 Location/Qualifiers
source                  1..27
                        mol_type = other DNA
                        note = Primer P10SKP1F
                        organism = synthetic construct
SEQUENCE: 32
tttgctagca tggcggccga ggcggag                                      27

SEQ ID NO: 33           moltype = DNA   length = 29
FEATURE                 Location/Qualifiers
source                  1..29
                        mol_type = other DNA
                        note = Primer P10SKP1R
                        organism = synthetic construct
SEQUENCE: 33
tttggtacct cattcgaagg cccactggt                                    29

SEQ ID NO: 34           moltype = DNA   length = 58
FEATURE                 Location/Qualifiers
source                  1..58
                        mol_type = other DNA
                        note = Primer GWRBX1F
                        organism = synthetic construct
SEQUENCE: 34
ggggacaagt ttgtacaaaa aagcaggctt tatgtcggcc atggagaccg acatcaac    58

SEQ ID NO: 35           moltype = DNA   length = 55
FEATURE                 Location/Qualifiers
source                  1..55
```

```
                              mol_type = other DNA
                              note = Primer GWRBX1R
                              organism = synthetic construct
SEQUENCE: 35
ggggaccact tgtacaaga aagctgggtt ctagtgccca tatttctgaa attcc          55

SEQ ID NO: 36                 moltype = DNA   length = 29
FEATURE                       Location/Qualifiers
source                        1..29
                              mol_type = other DNA
                              note = Primer P10RBX1F
                              organism = synthetic construct
SEQUENCE: 36
tttgctagca tgtcggccat ggagaccga                                      29

SEQ ID NO: 37                 moltype = DNA   length = 30
FEATURE                       Location/Qualifiers
source                        1..30
                              mol_type = other DNA
                              note = Primer P10RBX1R
                              organism = synthetic construct
SEQUENCE: 37
tttggtaccc tagtgcccat atttctgaaa                                     30

SEQ ID NO: 38                 moltype = DNA   length = 54
FEATURE                       Location/Qualifiers
source                        1..54
                              mol_type = other DNA
                              note = Primer GWGID2F
                              organism = synthetic construct
SEQUENCE: 38
ggggacaagt ttgtacaaaa aagcaggctt tatgaagttc cgctctgatt cgtc          54

SEQ ID NO: 39                 moltype = DNA   length = 55
FEATURE                       Location/Qualifiers
source                        1..55
                              mol_type = other DNA
                              note = Primer GWGID2R
                              organism = synthetic construct
SEQUENCE: 39
ggggaccact tgtacaaga aagctgggtt ctacccgcat tggccccctc cattc          55

SEQ ID NO: 40                 moltype = DNA   length = 34
FEATURE                       Location/Qualifiers
source                        1..34
                              mol_type = other DNA
                              note = Primer PHGID2FF
                              organism = synthetic construct
SEQUENCE: 40
tttgaattca tgaagttccg ctctgattcg tcag                                34

SEQ ID NO: 41                 moltype = DNA   length = 63
FEATURE                       Location/Qualifiers
source                        1..63
                              mol_type = other DNA
                              note = Primer PHGID2FR
                              organism = synthetic construct
SEQUENCE: 41
ttttctagat cacttgtcgt catcgtcttt gtagtccccg cattggcccc ctccattctt    60
atc                                                                  63

SEQ ID NO: 42                 moltype = DNA   length = 40
FEATURE                       Location/Qualifiers
source                        1..40
                              mol_type = other DNA
                              note = Primer PHD53INF
                              organism = synthetic construct
SEQUENCE: 42
catcgggcgc ggatccatgc ccactccggt ggccgccgcg                          40

SEQ ID NO: 43                 moltype = DNA   length = 68
FEATURE                       Location/Qualifiers
source                        1..68
                              mol_type = other DNA
                              note = Primer PHD53INHAR
                              organism = synthetic construct
SEQUENCE: 43
gtaggccttt gaattctcaa gcgtaatctg gaacatcgta tgggtaacaa tctagaatta    60
ttcttggc                                                             68
```

```
SEQ ID NO: 44          moltype = DNA  length = 40
FEATURE                Location/Qualifiers
source                 1..40
                       mol_type = other DNA
                       note = Primer PHHsSic1F
                       organism = synthetic construct
SEQUENCE: 44
cgacgagctc actagtatgg acgggactat taaggaggct                           40

SEQ ID NO: 45          moltype = DNA  length = 70
FEATURE                Location/Qualifiers
source                 1..70
                       mol_type = other DNA
                       note = Primer PHHsSic1HAR
                       organism = synthetic construct
SEQUENCE: 45
gactgcaggc tctagatcaa gcgtaatctg gaacatcgta tgggtagtag tagctgccta     60
agtgtgaagg                                                            70
```